(12) United States Patent
Penning et al.

(10) Patent No.: US 9,228,226 B2
(45) Date of Patent: Jan. 5, 2016

(54) MITOCHONDRION-BOUND NUCLEIC ACID FOR DETERMINING A HEALTH STATUS OF AN INDIVIDUAL

(75) Inventors: Maarten T. Penning, Utrecht (NL); Henriette C. G. I. M. Maas, Amsterdam (NL); Marinus P. de Baar, Amsterdam (NL); Emile E. Voest, Soest (NL)

(73) Assignees: Primagen Holding B.V., Amsterdam (NL); UMC Utrecht Holding B.V., Utrecht (NL)

( * ) Notice: Subject to any disclaimer, the term of this patent is extended or adjusted under 35 U.S.C. 154(b) by 404 days.

(21) Appl. No.: 12/317,907

(22) Filed: Dec. 29, 2008

(65) Prior Publication Data

US 2009/0317814 A1 Dec. 24, 2009

Related U.S. Application Data

(63) Continuation of application No. 12/150,963, filed on May 2, 2008, now abandoned, which is a continuation of application No. 11/666,632, filed as application No. PCT/NL2005/000771 on Oct. 28, 2005, now abandoned.

(60) Provisional application No. 60/658,114, filed on Mar. 3, 2005, provisional application No. 60/623,845, filed on Oct. 29, 2004.

(30) Foreign Application Priority Data

Oct. 29, 2004 (EP) .................................... 04077978
Mar. 3, 2005 (EP) .................................... 05075531

(51) Int. Cl.
*C12Q 1/68* (2006.01)

(52) U.S. Cl.
CPC ................ *C12Q 1/68* (2013.01); *C12Q 1/6865* (2013.01)

(58) Field of Classification Search
None
See application file for complete search history.

(56) References Cited

U.S. PATENT DOCUMENTS

| 6,344,322 B1 * | 2/2002 | Polyak et al. ................... 435/6 |
| 6,489,095 B2 | 12/2002 | Herrnstadt et al. |
| 6,967,016 B2 | 11/2005 | van Gemen et al. |
| 2005/0208549 A1 | 9/2005 | van Gemen et al. |
| 2006/0241033 A1 * | 10/2006 | Burzio et al. ................... 514/12 |

FOREIGN PATENT DOCUMENTS

| EP | 1 229 130 A2 | 8/2002 |
| EP | 1 325 963 A1 | 7/2003 |
| EP | 1 418 241 A1 | 5/2004 |
| WO | WO 97/42344 | 11/1997 |
| WO | WO 99/66075 | 12/1999 |
| WO | WO 00/11219 A1 | 3/2000 |
| WO | WO 02/46470 A2 | 6/2002 |
| WO | WO 03/080869 A2 | 10/2003 |

OTHER PUBLICATIONS

Lim et al, Mitochondrion, 2001, 1:71-77.*
Chiu et al, Clinical Chemistry, 2003, 49:719-726.*
Spitzer et al, Int J Cancer, 2000, 85:474-48.*
Beheshti et al, Neoplasia, 2003, 5:53-62.*
Boultwood et al, Br J Haematol, 1996, 95:426-431.*
Haugen et al, Thyroid, 2003, 7:613-620.*
PCT International Search Report, PCT/NL2005/000771, dated Jun. 29, 2006.
Database Medline, US National Library of Medicine, Bethesda, MD, US, Apr. 2000, Gadre et al., Comparative study of alkaline phosphate and prostate specific antigen in prostate cancer, XP002384815, and Indian Journal of Medical Sciences, Apr. 2000, pp. 136-139, vol. 54, No. 4.
Lievre et al., Clinical value of mitochondrial mutations in colorectal cancer, Journal of Clinical Oncology: Official Journal of the American Society of Clinical Oncology, May 20, 2005, pp. 3517-3525, vol. 23, No. 15.

* cited by examiner

*Primary Examiner* — Mark Halvorson
(74) *Attorney, Agent, or Firm* — TraskBritt, P.C.

(57) ABSTRACT

The invention describes means and methods for determining mitochondrion-bound nucleic acid and describes the use thereof in diagnostics. Preferable cell-free mitochondrion-bound nucleic acid is determined.

29 Claims, 36 Drawing Sheets

Effect of centrifugation on mtDNA and mtRNA quantification (averaged)

Effect of centrifugation on U1A quantification mtDNA quantification in non-centrifugated breast cancer samples mtRNA quantification in non-centrifugated breast cancer samples mtDNA quantification in centrifugated breast cancer samples mtRNA quantification in centrifugated breast cancer samples mtRNA quantification in non-centrifugated prostate cancer samples mtDNA quantification in centrifugated prostate cancer samples mtDNA quantification in healthy volunteers and patients with renal cell carcinoma mtRNA quantification in healthy volunteers and patients with renal cell carcinoma mtDNA and mtRNA copy numbers are significantly increased in the plasma of patients with prostate cancer compared to individuals with benign lesions of the prostate (p=0.002 and p=0.026)

mtDNA and mtRNA copy numbers in patients stratified to tumor growth mtDNA and mtRNA copy numbers in survivors and non-survivors plasma mtDNA in benign prostate disease and prostate cancer two-spin plasma plasma mtRNA in benign prostate disease and prostate cancer two-spin plasma Three-year survival in patients with higher vs. lower mtDNA and mtRNA copy numbers mtDNA and mtRNA copy numbers are (not significantly) increased in the plasma of patients with breast cancer compared to individuals with benign lesions of the breast plasma mtDNA in healthy individuals and cancer patients
two-spin plasma plasma mtRNA in healthy individuals and cancer patients
two-spin plasma mtDNA and mtRNA in patients with bone metastasis mtDNA is increased in patients with bone metastasis
two-spin plasma mtRNA is increased in patients with bone metastasis
two-spin plasma p=0.04

Kaplan-Meier survival analysis in patients with breast cancer for high or low plasma mtDNA mtDNA and mtRNA in plasma from healthy controls
and RCC patients mtDNA and mtRNA copy numbers in RCC patients before and after treatment plasma mtDNA in stage IV RCC patients treated with Atrasentan plasma mtRNA in stage IV RCC patients treated with Atrasentan MITOCHONDRION-BOUND NUCLEIC ACID FOR DETERMINING A HEALTH STATUS OF AN INDIVIDUAL

CROSS-REFERENCE TO RELATED APPLICATION

This application is a continuation of U.S. patent application Ser. No. 12/150,963, filed May 2, 2008, now abandoned, which application is a continuation of U.S. patent application Ser. No. 11/666,632, filed Apr. 27, 2007, now abandoned, which is a National Phase Entry of PCT International Patent Application No. PCT/NL2005/000771, filed on Oct. 28, 2005, designating the United States of America, and published in English as PCT International Publication No. WO 2006/062389 A2 on Jun. 15, 2006, and claims the benefit, under 37 U.S.C. §119(e) of U.S. Provisional Patent Application Ser. No. 60/658,114, filed Mar. 3, 2005, and U.S. Provisional Patent Application Ser. No. 60/623,845, filed Oct. 29, 2004. The application also claims priority to EP 05075531.3, filed Mar. 3, 2005, and EP 04077978.7, filed Oct. 29, 2004. The contents of all of which are incorporated herein by this reference.

TECHNICAL FIELD

The invention relates to the field of medicine and diagnostics therefor. The invention in particular relates to the diagnostics for determining a health status of an individual.

BACKGROUND

The field of diagnostics is rapidly expanding. With increasing knowledge of diseases, more and more refined diagnostic tools are becoming available. These diagnostics typically use specific characteristics of a disease. These specific characteristics are, more often than not, genetic characteristics. These can be monitored on the protein level or on the nucleic acid level. Current trends are toward very precise diagnostics using specific genetic markers or antibodies or brute force methods using arrays of many different specific markets. These tests are very often designed to ever more finely discriminate between diseases and individuals. This increasing discrimination power often means that individuals are screened several times with increasingly refined diagnostic tests.

Methods of the present invention provide information at the top of this diagnostic cascade and are simple enough to incorporate in routine health screenings and check-ups. To this end, the invention provides a method for determining a health status of an individual comprising determining mitochondrion-bound nucleic acid in a sample of body fluid or feces of an individual. Body fluid and feces contain mitochondria. These mitochondria are probably ultimately destined to be destroyed. However, they are sufficiently intact to allow the determination of nucleic acid that is contained therein or associated therewith. Mitochondrion-bound nucleic acid is determined and the amount detected is indicative for the health status of the individual.

With "mitochondrion-bound nucleic acid" is, therefore, meant nucleic acid that is present in mitochondria or associated therewith. Mitochondrion-bound nucleic acid comprises at least one sequence of a nucleic acid that is normally present in mitochondria from the species of the individual that the sample is derived from. Other nucleic acid may be associated with (cell-free) mitochondria as produced in the present invention. However, such other nucleic acid, for instance, nucleic acid comprising a sequence that is normally found in the nucleus of a cell of the species that the individual belongs to, is not mitochondrion-bound nucleic acid as defined in the present invention.

Body fluid, such as lymph fluid, blood, urine, brain fluid or saliva also contains cells that also contain mitochondria. In the present invention, it is preferred that cell-free mitochondrion-bound nucleic acid is determined. "Cell-free" in this context means that mitochondria that are associated with cells, either internal to or linked thereto, are not considered.

Cell-free mitochondrion-bound nucleic acid can be determined in various ways. One way is to determine the amount of total mitochondrion-bound nucleic acid and the amount of cellular mitochondrion-bound nucleic acid in the sample and subtracting the amount of cellular mitochondrion-bound nucleic acid from the amount of total mitochondrion-bound nucleic acid. However, in samples that are rich in cells (such as blood), it is preferred that cellular mitochondria are essentially removed from the sample prior to determining cell-free mitochondrion-bound nucleic acid. Removal is typically done by utilizing the difference in density and/or size of the mitochondrion compared to intact cells. However, more specific means, such as antibody-based separation methods, are also possible.

DISCLOSURE OF THE INVENTION

In a preferred embodiment, essentially cell-free mitochondrion-bound nucleic acid is obtained by centrifuging the sample. It is not necessary to quantitatively separate cells (cellular mitochondria) from mitochondria. With "essentially free," it is, therefore, meant for practical purposes free of cellular mitochondria. A sample that is made essentially mitochondria free has undergone at least one step wherein cells are preferentially removed from the sample. Centrifugation is one of such preferred means. Normally, cells are pelleted by centrifugation at 1700×g for 15 or 30 minutes. However, a preferred range of centrifugation is between 1600 and 1800×g (or rcf). For further purification of the cell-free mitochondrial fraction from cellular mitochondria, an additional centrifugation step with a g-force of between 2500 and 4500 g, preferably between 3000 and 4000 g, more preferably about 3400 g, is preferred.

Samples could be frozen and subsequently centrifuged to remove residual cells. Such samples were particularly suited for determining whether the individual was suffering from tumors and/or metastasis. Freezing apparently did not affect the density and sedimentation characteristics of the mitochondria. Thus, in a particularly preferred embodiment, a sample from the individual can be made essentially cell free, preferably by means of centrifugation, and frozen. After thawing, the sample is used in a method of the invention directly or the sample can be centrifuged and subsequently used in a method of the invention. Thus, in another particularly preferred embodiment, a sample from the individual is not made essentially cell free, and frozen. After thawing, the sample is centrifuged and subsequently used in a method of the invention. In yet another preferred embodiment, the sample is made essentially cell free, preferably by means of centrifugation between 1600 and 1800×g for sufficient time to allow sedimentation of cells prior to being frozen, subsequently frozen and thereafter thawed and centrifuged again, preferably at least at 1600 g.

Preferably, the second centrifugation is performed at a g-force of between 2500 and 4500 g, preferably between 3000 and 4000 g, more preferably at about 3400 g. Centrifugation times are herein set at 15 to 30 minutes; however, the time of centrifugation is not critical in the sense that centrifugation should be at least long enough to allow sedimentation of cells. This depends, among others, on the length of the of fluid column through which the cells have to migrate. Overlong centrifugation is not desired as it increases the chance that the sample deteriorates. Typically, though not necessarily, centrifugation times of between 15 and 30 minutes are sufficient. However, this does not mean that shorter or longer centrifugation times are also suitable, depending on the circumstances such as the length of the fluid column through which cells have to sediment.

As quality control for the amount of cell-bound mitochondria, it is preferred that additionally a nuclear nucleic acid is determined. The result obtained with this measurement (amplification) is preferably used to verify that the amount of nucleic acid from cell-bound mitochondria is negligible in a method of the invention, i.e., to verify the relative freeness of the sample for cells. This quality control is preferably performed in so-called duplex reactions in the same tube.

Methods for quantitating mitochondrial nucleic acid are described herein. Further methods and methods for quantitating mitochondrial nucleic acid in a so-called duplex assay wherein two or more different nucleic acids are amplified simultaneously are described in WO 02/46470, which is incorporated by reference herein.

Both DNA and RNA can be determined in a method of the present invention. It is preferred that the mitochondrion-bound nucleic acid comprises RNA. Although RNA is typically much less stable than DNA, it has been found that cell-free mitochondrion-bound RNA correlates more precisely with the health status of the individual. Determining the health status preferably comprises determining whether the individual is suffering from cancer. It has been found that a changed level of cell-free mitochondrion-bound nucleic acid is correlated with individuals that suffer from cancer. This finding is not limited to certain types of cancers. All types of cancer analyzed showed this correlation. In a preferred embodiment, cancer comprises ovarian, breast, prostate, RCC, colorectal, ENT or lung cancer. In this embodiment, it is preferred that the body fluid is blood, plasma, or serum. As blood, plasma or serum is also routinely collected from individuals that are tested for disease, it is preferred that the sample comprises blood, and preferably plasma or serum. Particularly for prostate cancer, the body fluid is preferably plasma or urine.

In a preferred embodiment, a method of the invention is used for providing a prognosis of an individual suffering from cancer. Individuals suffering from cancer with a poor survival prognosis have a markedly higher amount of mitochondrion-bound nucleic acid in samples of body fluid than individuals suffering from the same type of cancer but that have a good survival prognosis.

In this embodiment, mitochondrion-bound nucleic acid is determined in a sample obtained from an individual suffering from cancer, and the amount determined is used to determine the prognosis. Preferably, the amount is compared with a reference value. Preferably, the reference value is a value obtained from a collection of values of amounts of mitochondrion-bound nucleic acid in samples of individuals suffering from cancer and wherein, the values in the collection are correlated with the survival of the individuals. The reference value is preferably a value that divides the collection of values in two groups: one group having low values of amount of mitochondrion-bound nucleic acid in samples and that have a good survival prognosis and a group having high values of amount of mitochondrion-bound nucleic acid in samples and that have a poor prognosis.

An amount of mitochondrion-bound nucleic acid determined for a test sample obtained from an individual suffering from cancer can then be compared with the dividing reference value and classified as an amount that is indicative for a poor survival prognosis when the determined amount is higher than the dividing reference value or classified as an amount that is indicative for a good survival prognosis when the determined value is lower than the dividing reference value. In the clinic, survival prognosis is usually given as percent survival in a group of similar individuals after a certain number of years. A method of the invention can also be used to provide such a percentage of survival after a certain number of years. The actual determined dividing reference value varies with the type of cancer that is analyzed. For instance, using a preferred method of the invention, the dividing reference value is preferably between 8900 and 31000 for prostate cancer, whereas it is preferably between 160000 and 180000, preferably 170000 for breast cancer.

It is noted that it is possible to obtain derived values wherein amounts of mitochondrion-bound nucleic acid is correlated with another value in the sample, such as for instance, the amount of albumin, nuclear nucleic acid, PSA or alkaline phosphates in the sample. When such derived values are used, the reference value should reflect this as is common practice for the person skilled in the art. A sample may further be compared with a number of reference values. For instance, instead of dividing the collection of values in two groups, the collection may be divided in several groups, wherein several reference values indicate the division into the different groups.

Determining survival prognosis can be done on cancer patients receiving a range of different treatments. However, survival prognosis can also be used to determine a treatment regimen for an individual patient. For instance, an individual suffering from cancer with a poor prognosis can be given a different treatment then an individual suffering cancer with a good prognosis. In this embodiment, determining the health status thus comprises determining the prognosis for the individual suffering from cancer.

In another preferred embodiment, a method of the invention is used for determining whether an individual suffering from cancer comprises one or multiple tumor sites. Individuals suffering from cancer have varying numbers of tumor sites. Individuals having multiple tumor sites have a markedly higher amount of mitochondrion-bound nucleic acid in samples of body fluid than individuals with only one tumor site. In this embodiment, mitochondrion-bound nucleic acid is determined in a sample obtained from an individual suffering from cancer, and the amount determined is used to classify the sample as a sample from an individual with one tumor site or with multiple tumor sites. It is preferred that the amount is compared with a reference value. In this embodiment, determining the health status thus comprises determining whether the individual suffering from cancer comprises one or multiple tumor sites.

In a particularly preferred embodiment, the cancer is breast cancer. It has been found that samples from breast cancer patients have significantly higher levels of cell-free mitochondrion-bound nucleic acid than samples from healthy individuals.

In a preferred embodiment, the invention provides a method for determining whether an individual is suffering from metastasis comprising determining in a sample of the individual suffering from a cancer, cell-free mitochondrion-bound nucleic acid. In a preferred embodiment, the individual is suffering from breast and/or prostate cancer. In this embodiment, determining the health status thus comprises determining whether the individual suffering from cancer comprises metastasis or not.

In yet another preferred embodiment, determining the health status for an individual suffering from cancer comprises determining whether the individual comprises stable or progressive disease.

In yet another embodiment, a method according to the invention wherein the individual is suffering from cancer, is used to determine whether the individual is responding to treatment for cancer. In this embodiment, determining the health status thus comprises determining whether the individual responds to treatment. Preferably, the sample is a sample obtained after initiation of the treatment. Preferably, a determined amount of mitochondrion-bound nucleic acid in the sample is compared with a reference. Preferably, the reference is the amount of mitochondrion-bound nucleic acid in a sample obtained from the individual prior to initiation of treatment.

Other parameters in the sample may also be determined apart from mitochondrion-bound nucleic acid. This feature can be used to determine mitochondrion-bound nucleic acid relative to another parameter in the sample. This can be used to, for instance, standardize measurements. In a preferred embodiment, the other parameter comprises cell and mitochondrion-free nucleic acid. As this nucleic acid is typically subject to the extracellular environment of the sample, it is preferred that this nucleic acid is DNA, as DNA is typically more stable than RNA in such environments.

Other parameters can already be present in the sample or preferably can be added (spiked) prior to the determining mitochondrion-bound nucleic acid. Other parameters can also be used to strengthen predictive value of a method of the invention. As for any diagnostic method, there is always a chance that the test gives a false positive or false negative result. The chance thereof varies with the method. For cancer diagnostics in general, this chance is higher than for other types of diagnostics, for instance, pregnancy diagnostics.

Additional parameters can reduce the chance of giving a false negative or false positive result of a method of the invention. However, also tests that have a somewhat higher chance of giving a false positive or negative result are useful in everyday practice as such tests are often the only tests available for a certain diagnostic purpose. In addition, as already mentioned, such a test can be used in addition to other diagnostics and thereby reduce the chance of a false result. In one embodiment, the other parameter comprises PSA, alkaline phosphatase or a combination thereof.

In a preferred embodiment, mitochondrion-bound nucleic acid in the sample is compared with a reference. The reference can be a value for a healthy individual(s) and/or a value for individuals having a particular health status, such as suffering from cancer.

As the amounts of mitochondrion-bound nucleic acid in a cell-free sample is typically not very high it is preferred that the method comprises a nucleic acid amplification step for amplifying mitochondrion-bound nucleic acid. Examples of such amplification methods are PCR, NASBA, TMA, LCR, bDNA, rolling circle amplification and others. In a preferred embodiment, the amplification step comprises NASBA. Such amplification steps can be adapted such that they can quantitate the target nucleic acid in the sample. Quantitation is, therefore, preferred in a method of the invention. With "quantitation" is meant that the amount of mitochondrion-bound nucleic acid in the sample is determined. Although quantitation is preferred, it is also possible to determine whether mitochondrion-bound nucleic acid in the sample is higher or lower than a reference. In this case, assessment of the exact amount (quantitation) is not necessary.

The sample may be fluid. However, the body fluid may also be present in the sample in dried form. In dried form, the sample is more stable and does not require freezing or refrigeration. Thus, in a preferred embodiment, a sample of body fluid was dried and stored on a solid carrier prior to determining the amount of mitochondrion-bound nucleic acid. In a preferred embodiment, the solid carrier is paper. Suitable solid carriers such as paper are described in WO 03/080869, which is incorporated by reference herein. This reference is also referred to for methods for storing and recovering nucleic acid from the solid carrier.

Cellular mitochondrion-bound nucleic acid can also be another parameter. This parameter is tell-tale for a number of different diseases of individuals. It is, therefore, preferred that the results of cell-free mitochondrion-bound nucleic acid and cellular mitochondrion-bound nucleic acid are combined. As mentioned above, it is preferred that a method of the invention further comprises determining a non-mitochondrion-bound nucleic acid in the sample. This can be used, for instance, for standardization purposes. Thus, in one embodiment, the non-mitochondrion-bound nucleic acid is a control nucleic acid present in or provided to the sample.

In a preferred embodiment, the control nucleic acid and mitochondrion-bound nucleic acid is amplified in one amplification step. This so-called duplex analysis allows very accurate relative assessments of nucleic acid amounts.

The invention further provides a use of means for quantitating mitochondrion-bound nucleic acid in a sample of body fluid of an individual for determining whether the individual is suffering from cancer or, metastasizing of the tumor. It further provides a use of means for quantitating mitochondrion-bound nucleic acid in a sample of body fluid of an individual for predicting or following the effect of a cancer treatment in the individual suffering from cancer. The invention further provides a use of means for quantitating mitochondrion-bound nucleic acid in a sample of body fluid of an individual for predicting or determining side effects of a treatment. Changes in cell-free mitochondrion-bound nucleic acid are early events and precede clinical manifestations of side effects. In a preferred embodiment, quantitation comprises determining the time to positivity in an amplification reaction, preferably, the amplification reaction comprises NASBA.

The individual can be any mammal. In a preferred embodiment, the individual is a farm animal. In a particularly preferred embodiment, the individual is a human.

DETAILED DESCRIPTION OF THE INVENTION

Examples

Example 1

Healthy Donors Compared to Patients

Plasma was isolated from blood of healthy donors and patients with progressive cancer, using a BD Vacutainer® CPT™ Cell Preparation Tube with Sodium Citrate, according to the manufacturer's recommendations. The plasma samples were centrifuged at 3452 rcf for 15 minutes. The supernatant plasma was subsequently stored at −80° C. One hundred μl of plasma was added to a 1.5 ml Eppendorf tube containing 900 μl lysis buffer. The nucleic acid now present in the lysis buffer was further purified with the method described by Boom et al. (1990). The isolated nucleic acid was eluted in 50 μl elution buffer.

In Table 1, the primers and probes used in these examples are summarized. Standard NASBA nucleic acid amplification reactions were performed in a 20 μl reaction volume and contained: 40 mM Tris-pH 8.5, 90 mM KCl, 12 mM MgCl2, 5 mM dithiotreitol, 1 mM dNTPs (each), 2 mM rNTPs (each), 0.2 μM primer P1, 0.2 μM primer P2, 0.05 μM molecular beacon, 375 mM sorbitol, 0.105 μg/μl bovine serum albumin, 6.4 units AMV RT, 32 units T7 RNA polymerase, 0.08 units RNase H and input nucleic acid. For the amplification of RNA, the complete mixture (except the enzymes) was, prior to adding the enzymes, heated to 65° C. in order to denature any secondary structure in the RNA and to allow the primers to anneal. (In the case of DNA, 2 units of MSP II were added. The mix was incubated at 37° C. for 15 minutes, followed by denaturation at 95° C.) After cooling the mixture to 41° C., the enzymes were added. The amplification took place at 41° C. for 90 minutes in a thermostatted fluorimeter (CytoFluor® 2000 or EasyQ® Reader) and the fluorescent signal of the molecular beacon probe was measured every 45 seconds.

To achieve quantification, a dilution series of target sequence was amplified and the time points at which the reactions became positive (the time to positivity, TTP) were plotted against the input amounts of nucleic acid. This way, a calibration curve was created that could be used to read TTP values of reactions with unknown amounts of input and deduce the input amount. All amplifications were performed in duplicate. The average of these duplicate reactions was considered as the value for this sample. If the difference between duplicate amplifications was <0.5 log value, the value for this sample was considered "valid."

Figure 1A:
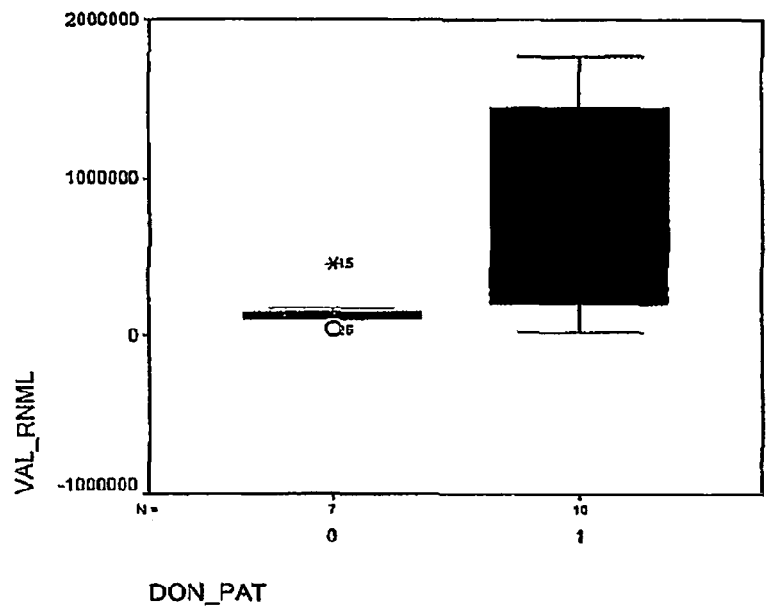
FIGS. 1A and 1B show mtRNA content in plasma from patients and healthy donors.
Figure 1B:
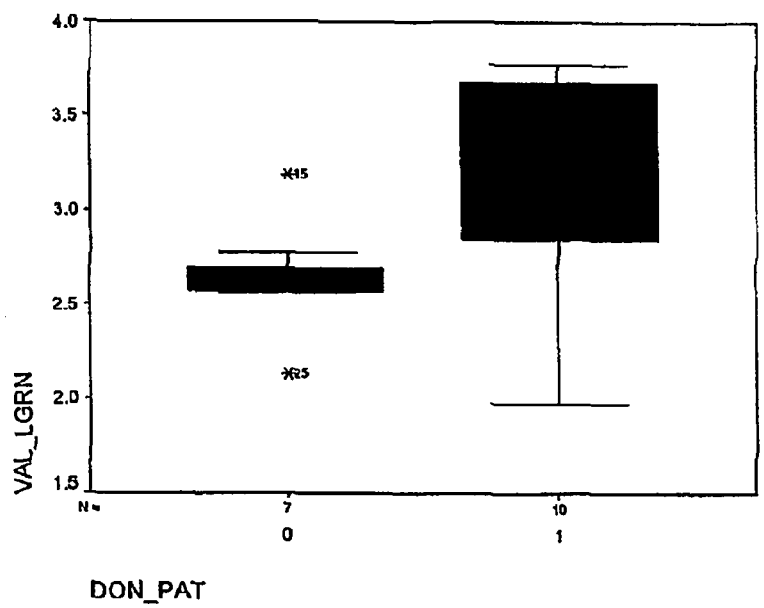
Figure 2A:
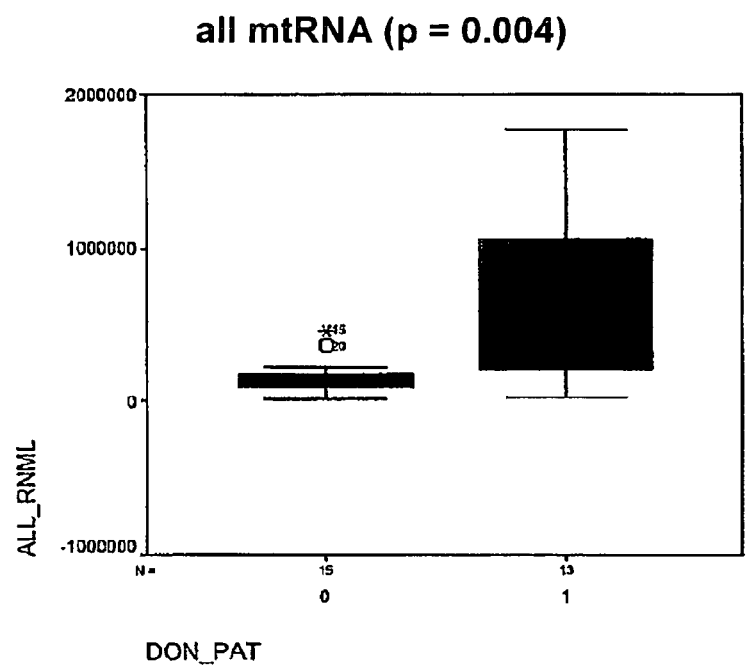
FIGS. 2A and 2B show mtRNA content in plasma from patients and healthy donors.
Figure 2B:
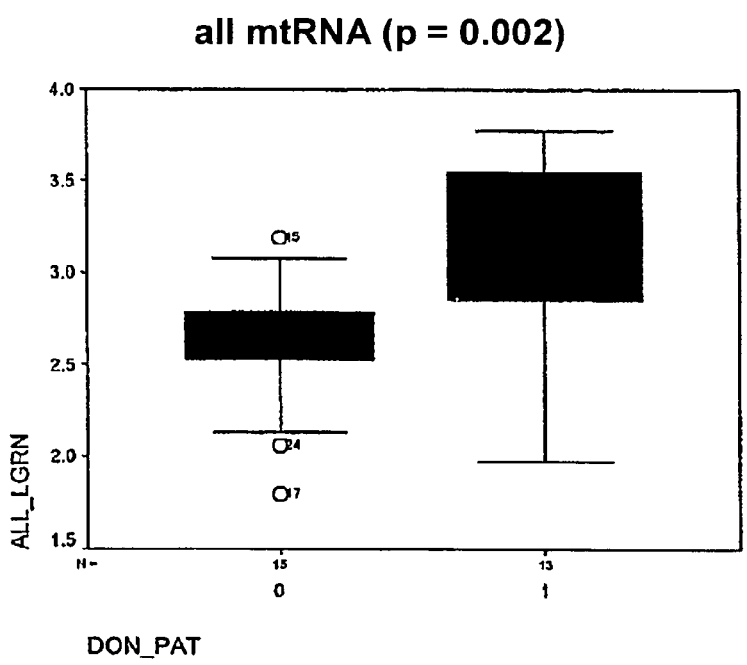

Analyzing the "valid" values, we find significantly higher mtRNA content in plasma from patients, compared to healthy donors (both when log values (FIG. 1A) or linear values (FIG. 1B) are compared). If we include the samples of which the difference between duplicates was more than 0.5 log, the significance became even stronger (FIGS. 2A and 2B), probably simply because more cases were included.

Figure 3A:
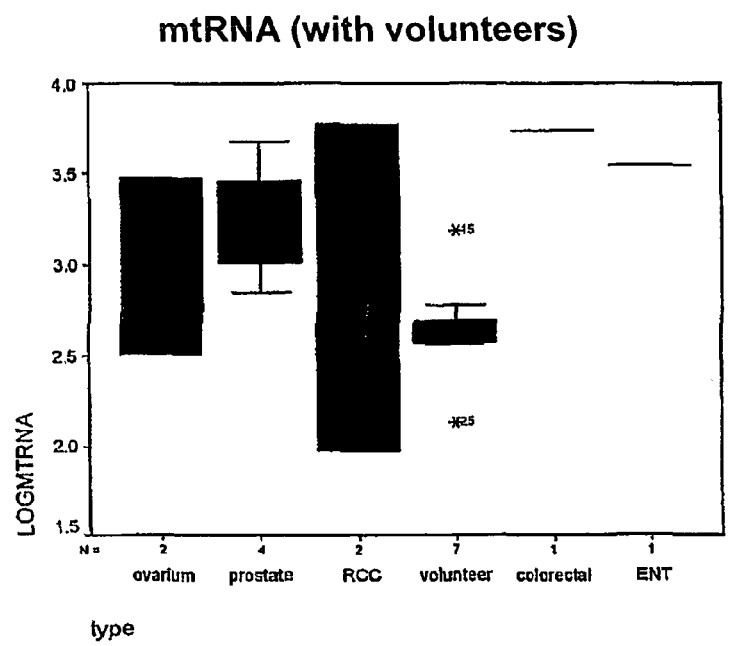
FIGS. 3A and 3B show mtRNA content in plasma from patients illustrated according to tumor type.
Figure 3B:
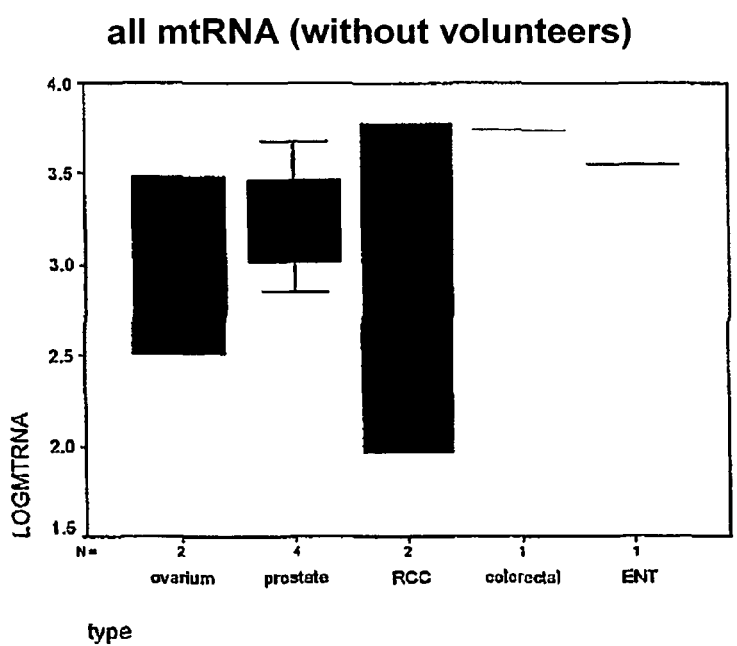
Figure 4A:
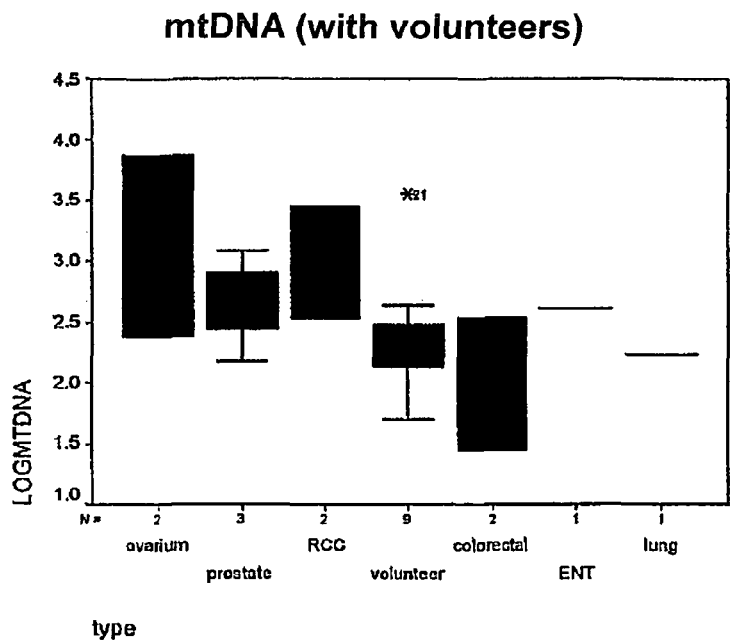
FIGS. 4A and 4B show mtDNA content in plasma from patients illustrated according to tumor type.
Figure 4B:
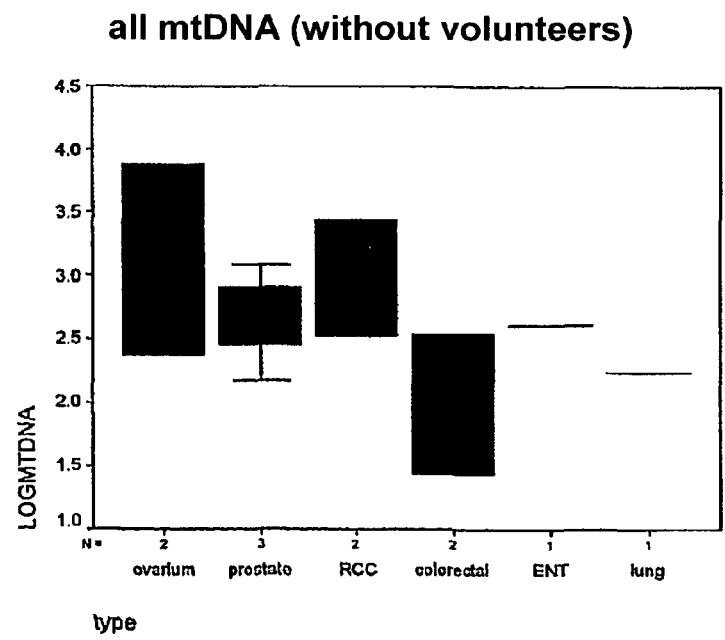
Figure 5A:
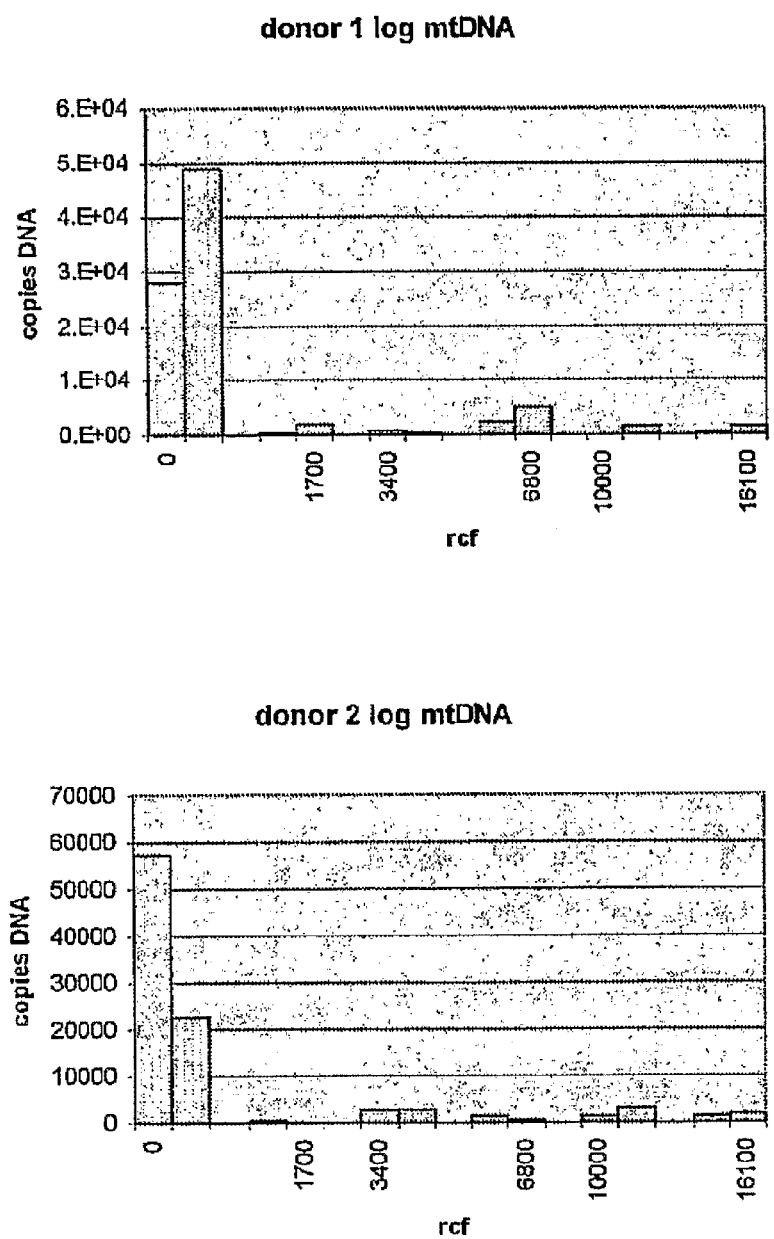
FIGS. 5A, 5B and 6A, 6B show the effects of centrifugation on mtDNA and mtRNA quantification of plasma.
Figure 5B:
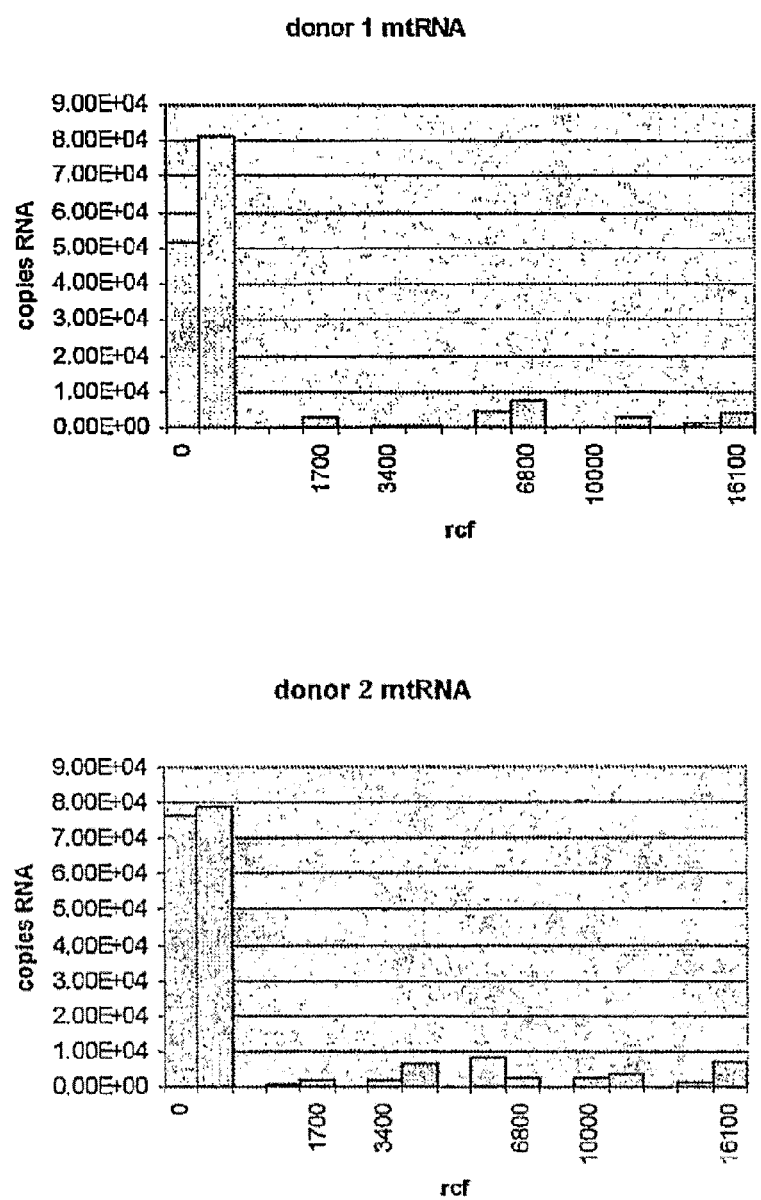
Figure 6A:
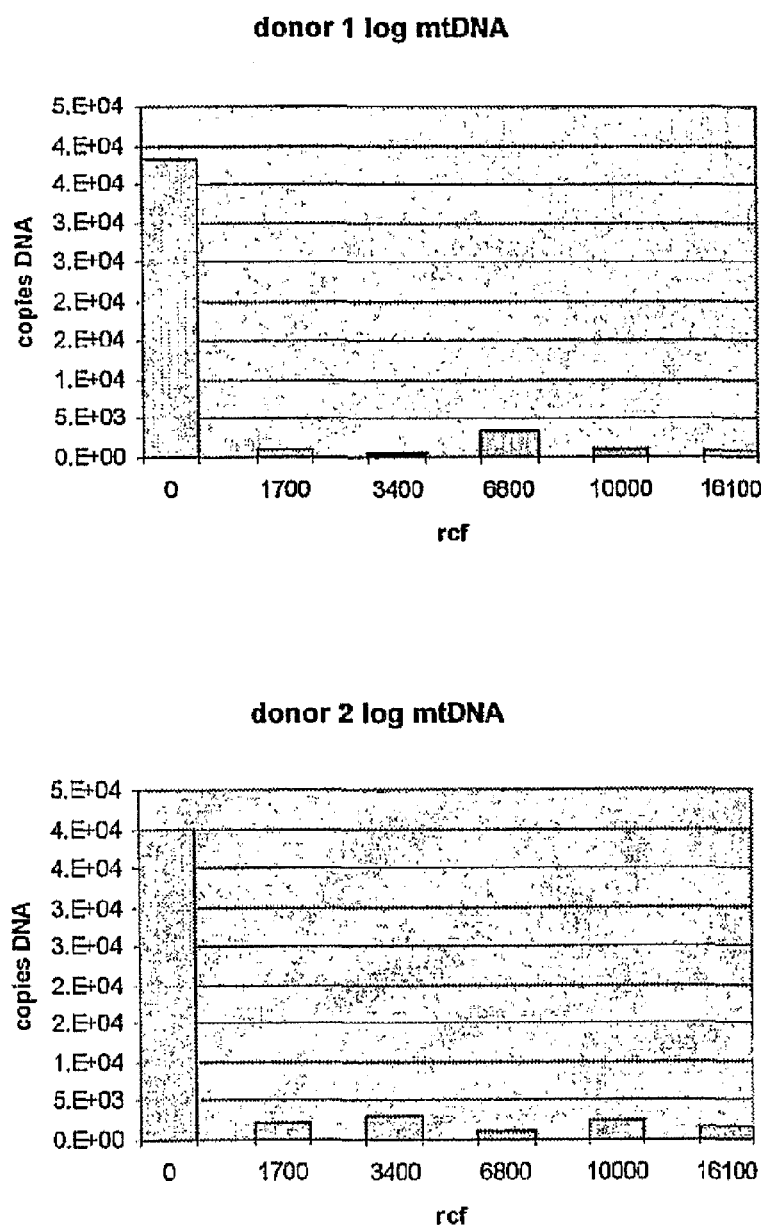
Figure 6B:
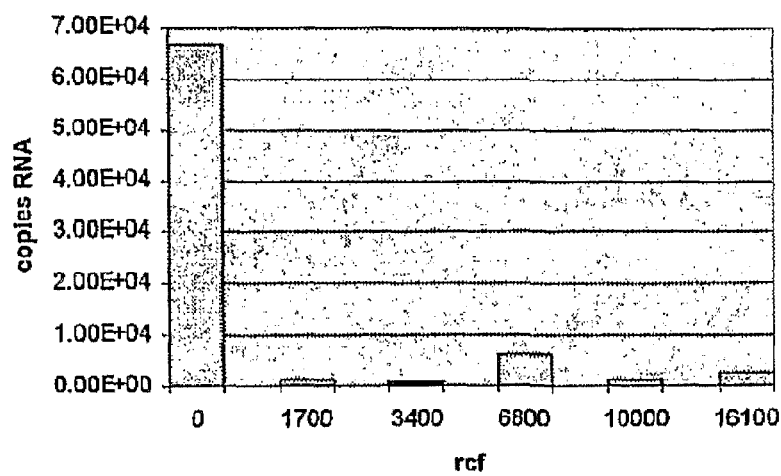
Figure 6B:
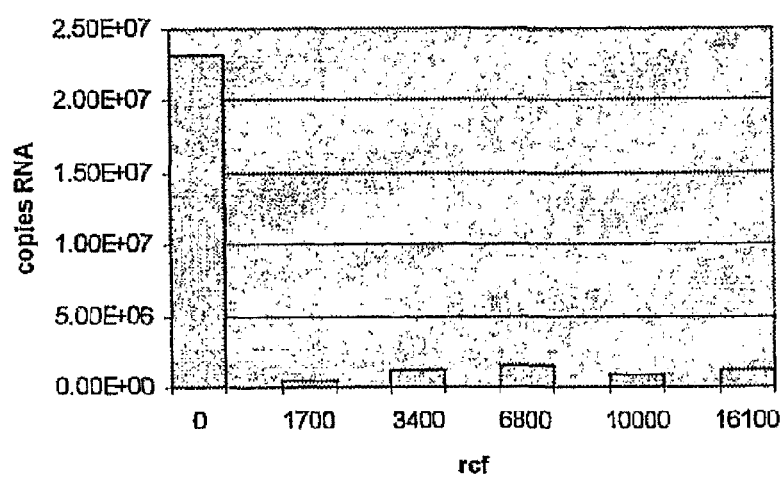

It is clear from FIGS. 1A, 1B and 2A, 2B that the variation in mtRNA is bigger in patients compared to healthy donors. Therefore, we split the samples according to tumor type and looked at mtRNA (FIGS. 3A, 3B) and mtDNA (FIGS. 4A, 4B).

In spite of the small number of patients in each group, it is clear that there are differences in mtRNA and/or mtDNA content in the plasma of patients suffering from different tumors.

Example 2

Centrifugation of Fresh Plasma

Different labs use different protocols to isolate plasma from blood. There are differences in blood collection tubes, the anti-coagulant used herein, and the handling time before blood is drawn, centrifuged and stored. Most laboratories use one centrifugation step to separate blood cells from plasma, but some laboratories perform an additional centrifugation step to get rid of residual cells (platelets) or cell debris. In this example the effect of this additional centrifugation step on the quantification of mtDNA, mtRNA and nuclear DNA (U1A) in plasma was investigated.

Plasma was isolated from the blood of two healthy male volunteers, using a BD Vacutainer® CPT™ Cell Preparation Tube with Sodium Citrate. Aliquots of 300 μl of the plasma were subjected to centrifugation at different speeds (0 rcf, 1700 rcf, 3400 rcf, 10000 rcf, and 16100 rcf). After centrifugation, 100 μl was added to a 900 μl lysis buffer in a 1.5 ml Eppendorf tube in duplo. The nucleic acid now present in the lysis buffer was further purified with the method described by Boom et al. (1990). The isolated nucleic acid was eluted in 50 µl elution buffer.

In Table 1, the primers and probes used in these examples are summarized. Standard NASBA nucleic acid amplification reactions were performed in a 20 µl reaction volume and contained: 40 mM Tris-pH 8.5, 90 mM KCl, 12 mM MgCl2, 5 mM dithiotreitol, 1 mM dNTPs (each), 2 mM rNTPs (each), 0.2 µM primer P1, 0.2 µM primer P2, 0.05 µM molecular beacon, 375 mM sorbitol, 0.105 µg/µl bovine serum albumin, 6.4 units AMV RT, 32 units T7 RNA polymerase, 0.08 units RNase H and input nucleic acid. For the amplification of RNA, the complete mixture (except the enzymes) was, prior to adding the enzymes, heated to 65° C. in order to denature any secondary structure in the RNA and to allow the primers to anneal. (In the case of DNA, 2 units of MSP II were added. The mix was incubated at 37° C. for 15 minutes, followed by denaturation at 95° C.) After cooling the mixture to 41° C., the enzymes were added. The amplification took place at 41° C. for 90 minutes in a thermostated fluorimeter (CytoFluor® 2000 or EasyQ® Reader) and the fluorescent signal of the molecular beacon probe was measured every 45 seconds.

To achieve quantification, a dilution series of target sequence was amplified and the time points at which the reactions became positive (the time to positivity, TTP) were plotted against the input amounts of nucleic acid. This way, a calibration curve was created that could be used to read TTP values of reactions with unknown amounts of input and deduce the input amount. All amplifications were performed in duplicate. The average of these duplicate reactions was considered as the value for this sample.

Figure 7:
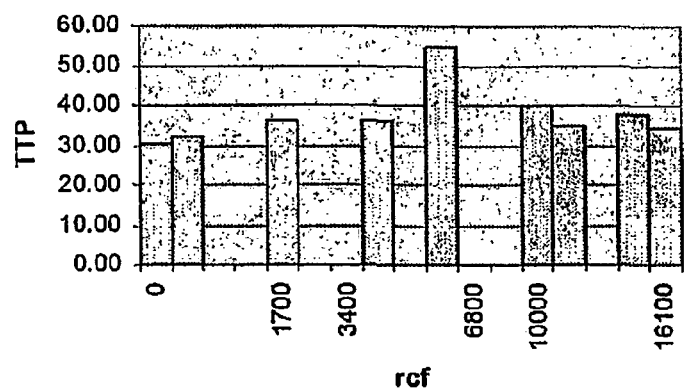
FIG. 7 shows the effects of centrifugation on U1A quantification.
Figure 7:
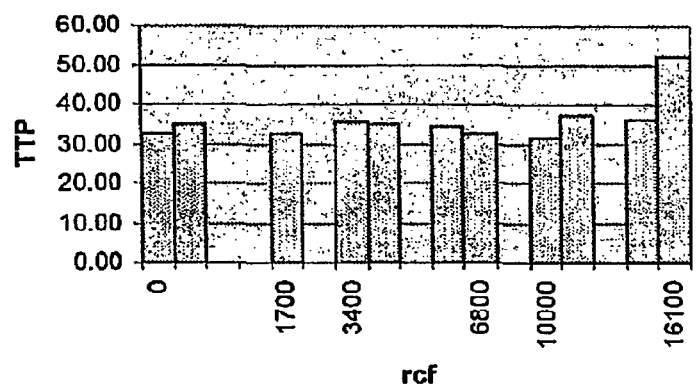

As shown in FIGS. 5A, 5B and 6A, 6B, an additional centrifugation step influences the result of mtRNA and mtDNA quantification of plasma significantly. Surprisingly, centrifugation at 1700 ref has the same effect as centrifugation at higher speeds. We would have expected to spin down residual cells at this lower speed and at higher speeds, free circulating mitochondria. To further address this possibility, U1A was also studied. Although U1A quantification was lower than the quantification limit in all samples, TTP values were plotted (FIG. 7). There seems to be no difference in the amount of U1A with or without centrifugation. This suggests that the plasma samples did not contain any residual cells. This also suggests that already at 1700 rcf, a part of the free-circulating mitochondria are spun down.

Example 3

Centrifugation of Frozen Plasma

As shown in Example 2, there is a clear effect on the quantification of mtDNA and mtRNA if the plasma undergoes an additional centrifugation step. In this example, it was investigated if a similar effect would be found if this additional centrifugation would be implemented after freezing at −80° C. and thawing of the plasma.

Plasma was isolated from the blood of a healthy volunteer, using a BD Vacutainer® CPT™ Cell Preparation Tube with Heparine. Aliquots of 300 µl of the plasma were subjected to different treatments, according to Table 2. After these treatments, two times 100 µl of each centrifuged plasma was added to a 900 µl lysis buffer in a 1.5 ml Eppendorf tube and stored at −80° C. The nucleic acid now present in the lysis buffer was further purified with the method described by Boom et al. (1990). The isolated nucleic acid was eluted in 50 µl elution buffer.

Figure 8:
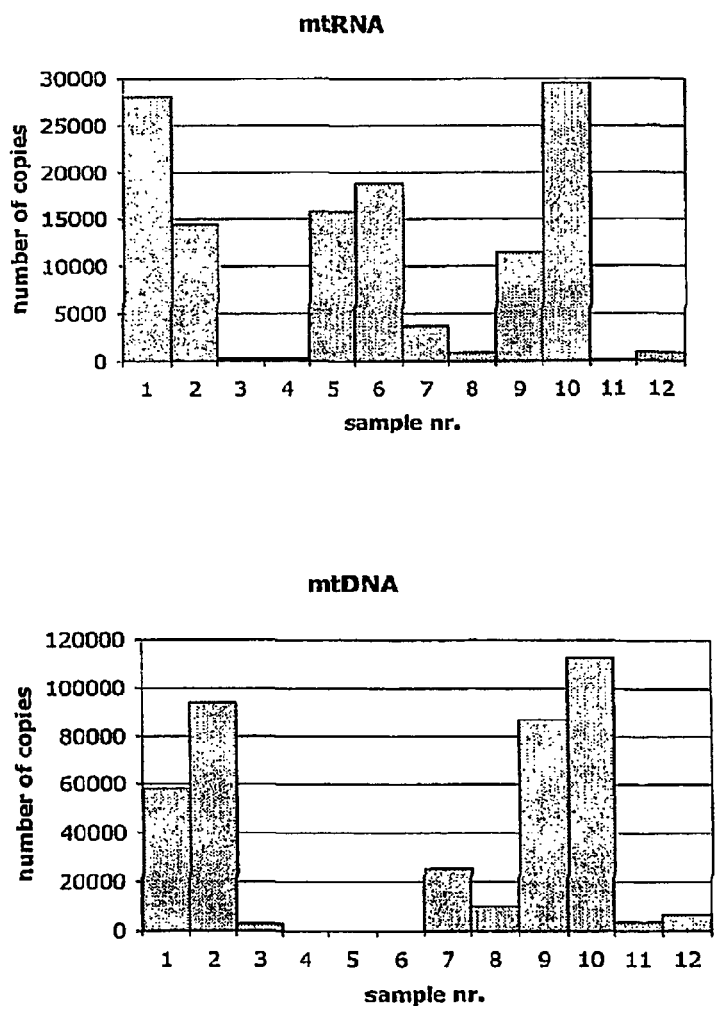
FIG. 8 shows the effects of quantification of mtRNA and mtDNA before and after freeze-thawing of samples.

After isolation, quantification of mtDNA and mtRNA was performed as described in Example 2. As is shown in FIG. 8, quantification seems to give similar results, independent if the plasma has been frozen or not. Also, the effect of centrifugation before and after freezing and thawing of the plasma seems to be similar. (mtDNA has not been quantified in samples 5 and 6.)

Example 4

Breast Cancer without Centrifugation

Plasma was isolated using a BD Vacutainer® CPT™ Cell Preparation Tube with Sodium Citrate. Two of those tubes were drawn, the first tube was discarded to avoid contamination of the blood draw. Plasma was isolated from eight female controls with benign breast disorders, seven patients with local breast cancer without distant metastasis, and 31 breast cancer with distant metastasis in bone or lung, as certified by radiological or histological examination. No additional centrifugation was applied to the plasma before storage at −80° C. After thawing, 100 µl of plasma was added to a 1.5 ml Eppendorf tube containing 900 µl lysis buffer. The nucleic acid now present in the lysis buffer was further purified with the method described by Boom et al. (1990). The isolated nucleic acid was eluted in 50 µl elution buffer. After isolation, quantification of mtDNA and mtRNA was performed as described in Example 2.

Figure 9:
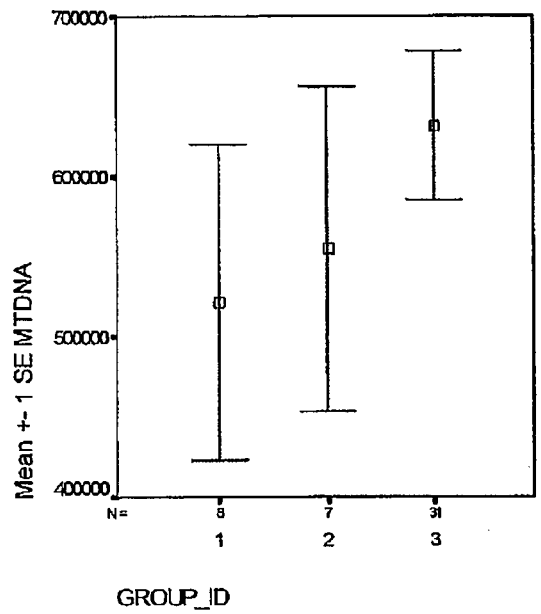
FIGS. 9 and 10 show mtDNA (FIG. 9) and mtRNA (FIG. 10) quantification in non-centrifugated breast cancer samples.
Figure 9:
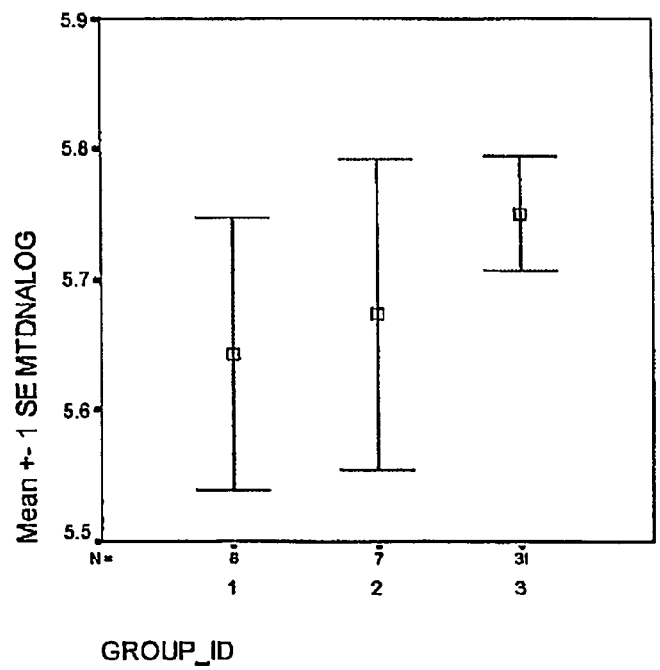
Figure 10:
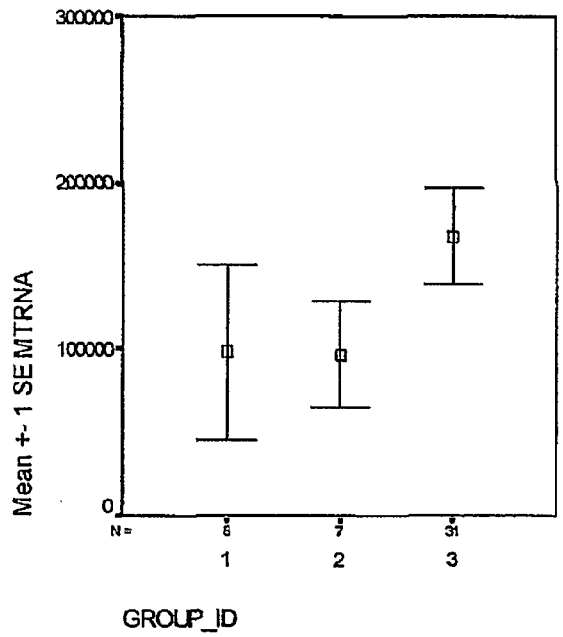
Figure 10:
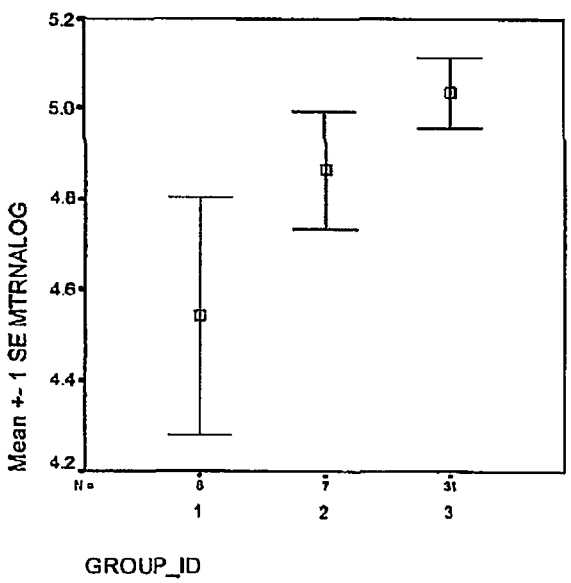

The results are summarized in FIGS. 9 (mtDNA) and 10 (mtRNA). A clear increase in copy numbers of mtDNA and mtRNA is observed in patients with metastasizing disease, compared to both other groups.

Figure 11:
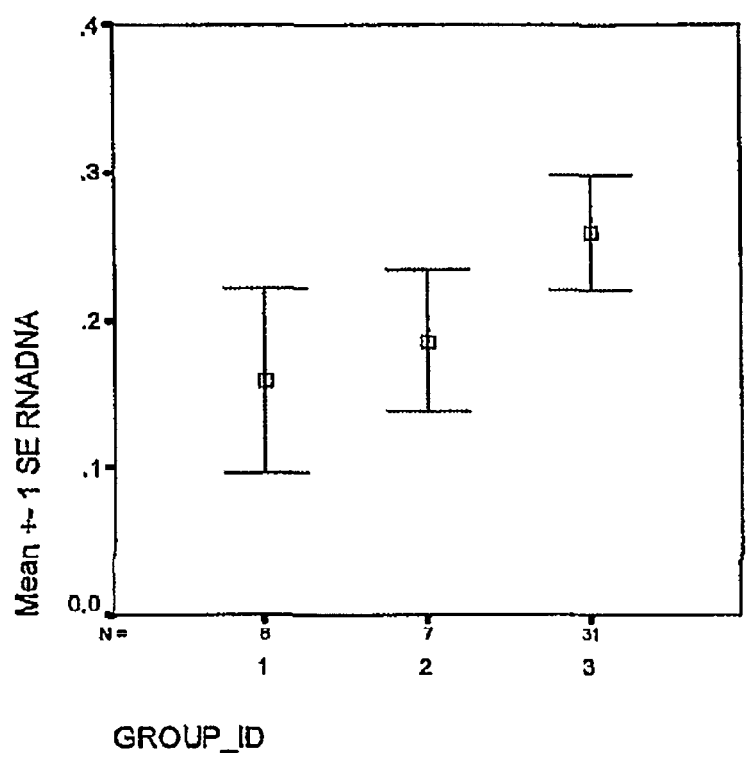
FIG. 11 shows mtRNA/mtDNA ratios in non-centrifugated breast cancer samples.

Also, the ratio of mtRNA/mtDNA is analyzed. Not only the copy number of mtDNA and mtRNA increase in patients with metastasizing breast tumors, also the ratio mtRNA/mtDNA increases in this group, as is clear from FIG. 11.

Example 5

Breast Cancer with Centrifugation

As shown in Examples 2 and 3, differences were found in quantification of mtDNA and mtRNA if plasma samples were centrifuged after they had been frozen at −80° C. Therefore, it was decided to centrifuge the samples described in Example 3 for 15 minutes at 3400 rcf, and put the upper 100 µl in 900 µl L6. Then, the nucleic acids were isolated and mtDNA and mtRNA were quantified as described in the previous examples.

Figure 12:
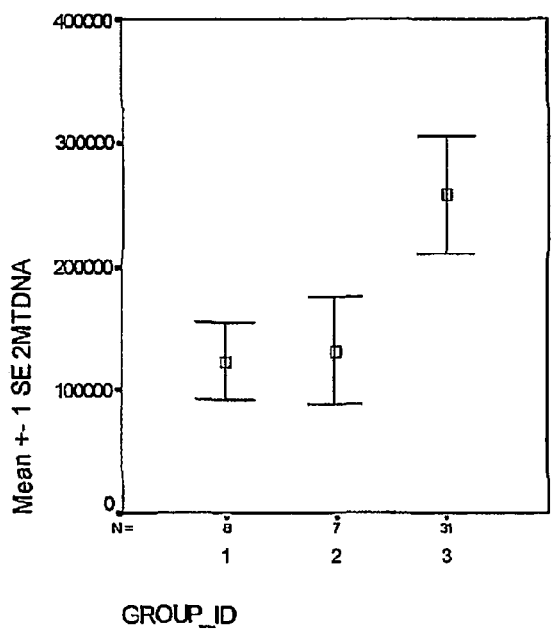
FIGS. 12 and 13 show mtDNA (FIG. 12) and mtRNA (FIG. 13) quantification in centrifugated breast cancer samples.
Figure 12:
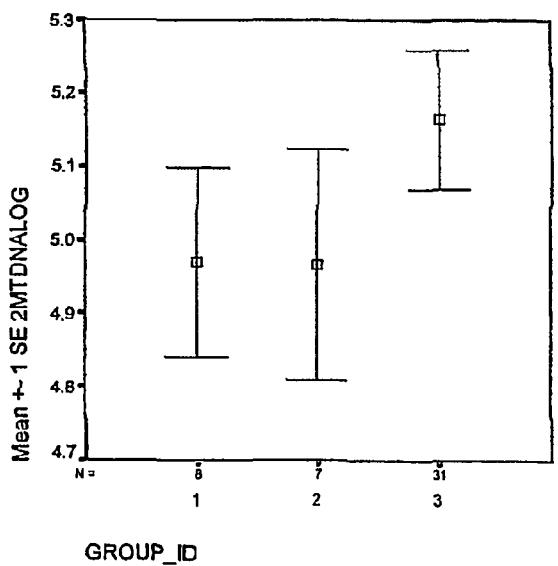
Figure 13:
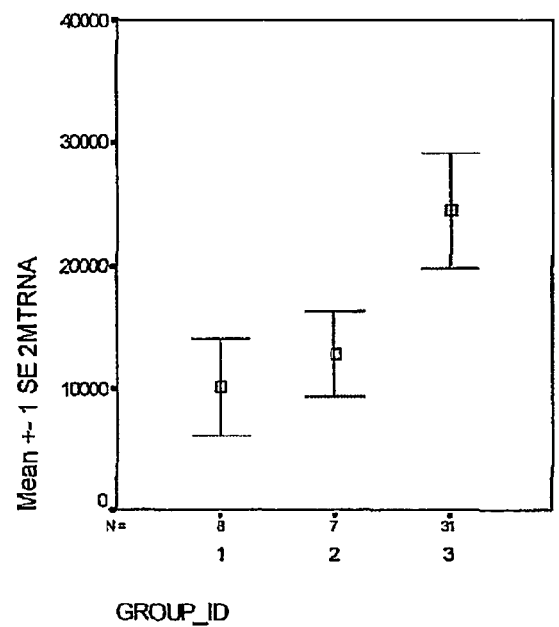
Figure 13:
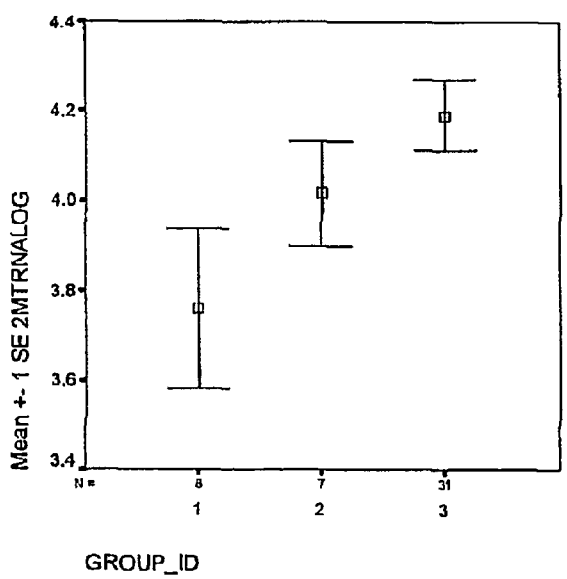

The results are summarized in FIGS. 12 (mtDNA) and 13 (mtRNA). A clear increase in copy numbers of mtDNA and mtRNA is observed in patients with metastasizing disease, compared to both other groups.

Figure 14:
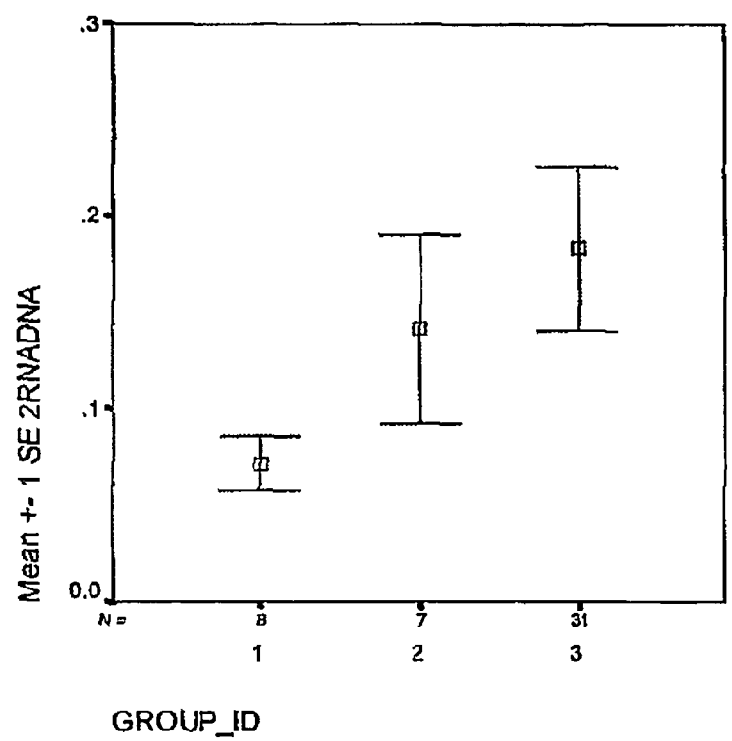
FIG. 14 shows mtRNA/mtDNA ratios in centrifugated breast cancer samples.

Also, the ratio of mtRNA/mtDNA is analyzed in the centrifuged plasma samples (FIG. 14). From this figure, it is clear that with our assays, it is possible to discriminate between patients with and without cancer.

Example 6

Prostate Cancer without Centrifugation

Plasma was isolated using a BD Vacutainer® CPT™ Cell Preparation Tube with Sodium Citrate. Two of those tubes were drawn, the first tube was discarded to avoid contamination of the blood draw. Plasma was isolated from 15 male controls with benign prostate hyperplasia, 15 patients with local prostate cancer without metastasis, and. 61 patients with prostate cancer with distant metastasis in bone or lung, as certified by X-ray, bone scintigraphy and/or histology. No additional centrifugation was applied to the plasma before storage at −80° C. After thawing, 100 µl of plasma was added to a 1.5 ml Eppendorf tube containing 900 µl lysis buffer. The nucleic acids were isolated and mtDNA and mtRNA were quantified as described in the previous examples.

Figure 15:
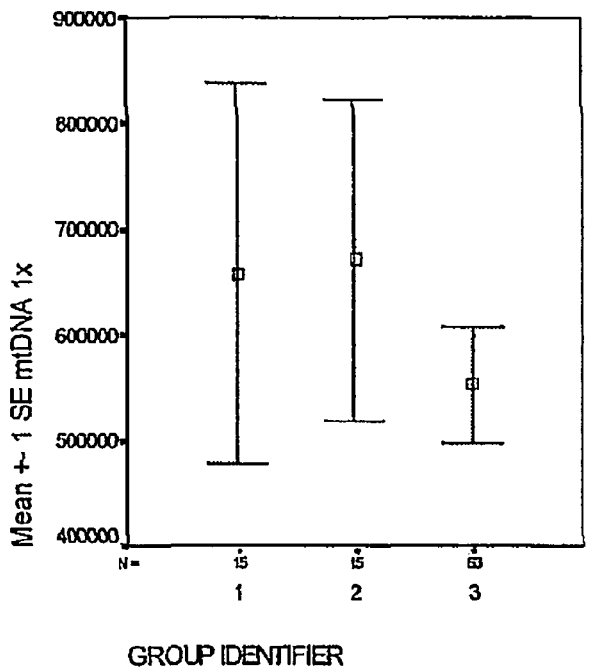
FIGS. 15 and 16 show mtDNA (FIG. 15) and mtRNA (FIG. 16) quantification in non-centrifugated prostate cancer samples.
Figure 15:
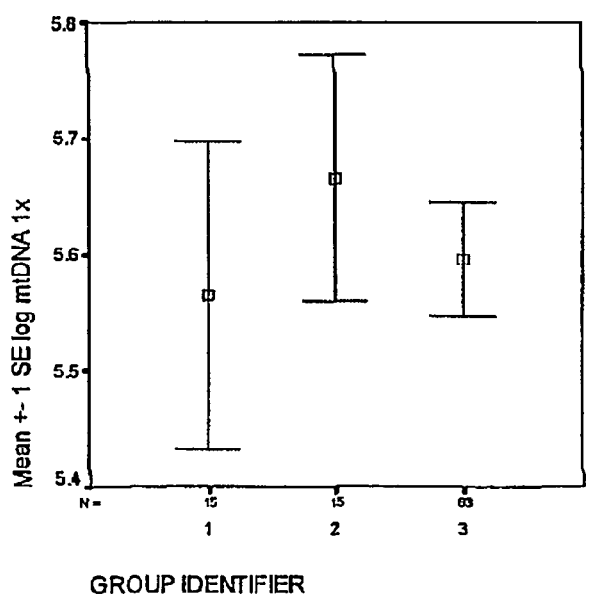
Figure 16:
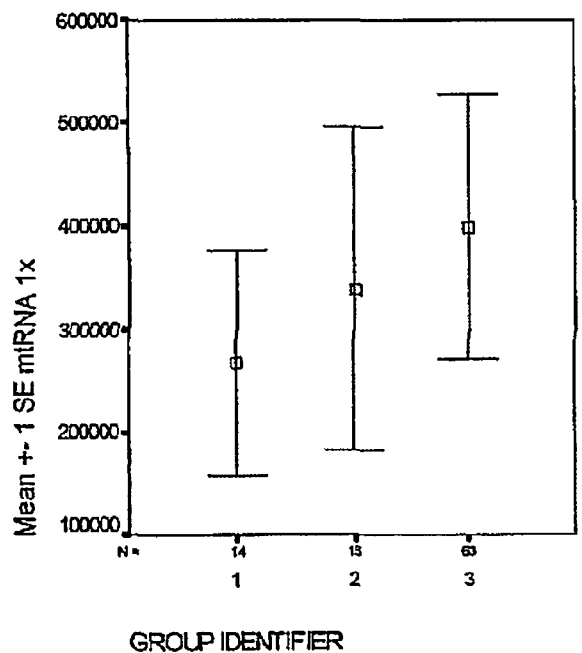
Figure 16:
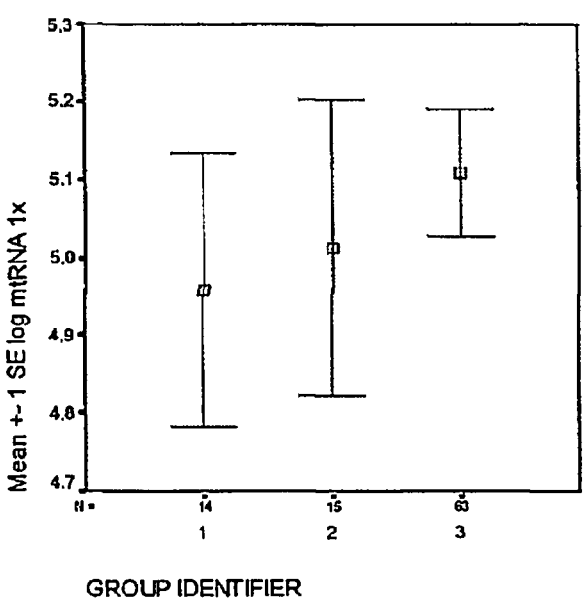

The results are summarized in FIGS. 15 (mtDNA) and. 16 (mtRNA). Especially in the case of mtRNA, average copy numbers differ between the three groups. In the case of mtDNA, the copy number in the group with metastasizing tumors differs from the other two.

Figure 17:
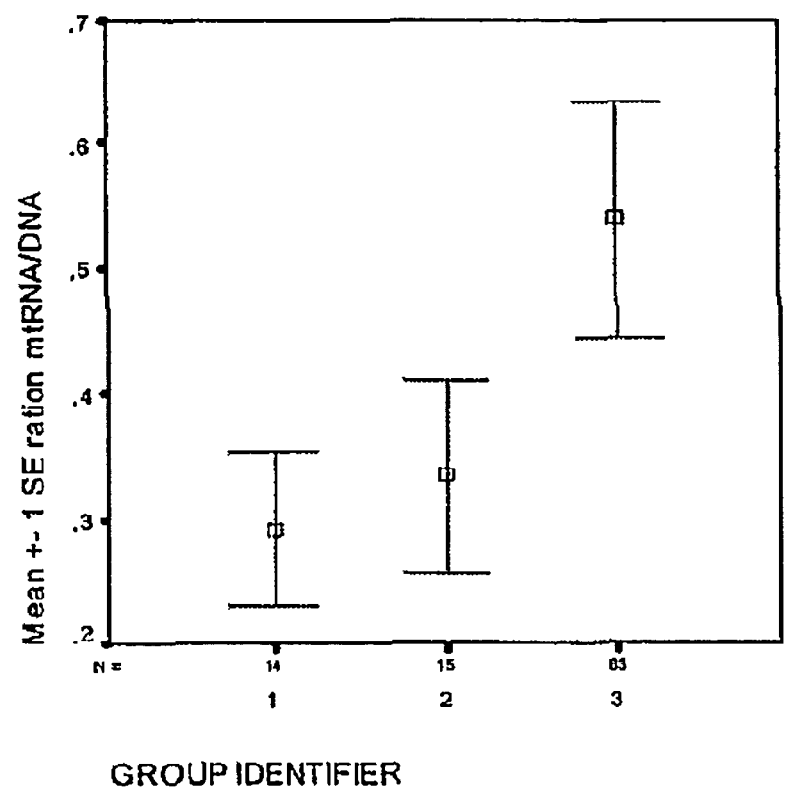
FIG. 17 shows mtRNA/mtDNA ratios in non-centrifugated prostate cancer samples.

When the mtRNA/mtDNA ratio is analyzed (FIG. 17), it is observed that the ratio increases in patients with local tumors as compared to patients with benign prostate hyperplasia. In the group of patients with metastasizing prostate tumors, the ratio increases even further. We expect these differences to become even more distinct after centrifugation of the plasma samples, as was also observed in breast cancer patients (Examples 4 and 5).

Example 7

Prostate Cancer with Centrifugation

As shown in Examples 4 and 5, differences were found in quantification of mtDNA and mtRNA if plasma samples were centrifuged after they had been frozen at −80° C. Therefore, the samples described in Example 6 were centrifuged for 15 minutes at 3400 rcf, and put the upper 100 µl in 900 µL6. Then, the nucleic acids were isolated and mtDNA and mtRNA were quantified as described in the previous examples.

Figure 18:
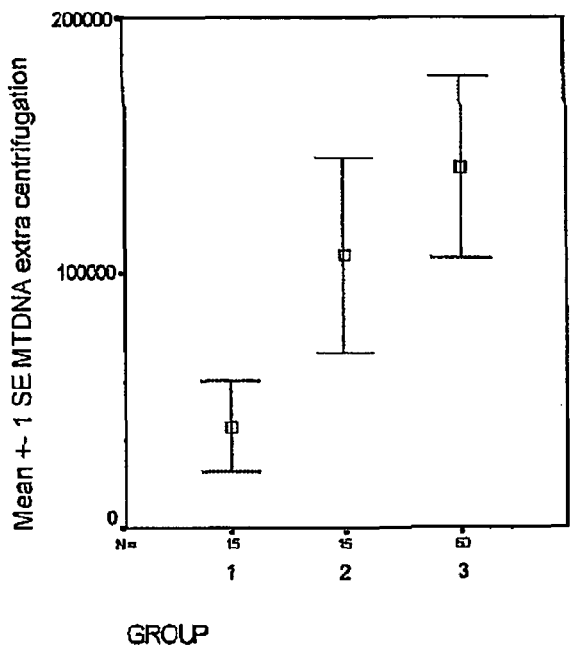
FIGS. 18 and 19 show mtDNA (FIG. 18) and mtRNA (FIG. 19) quantification in centrifugated prostate cancer samples.
Figure 18:
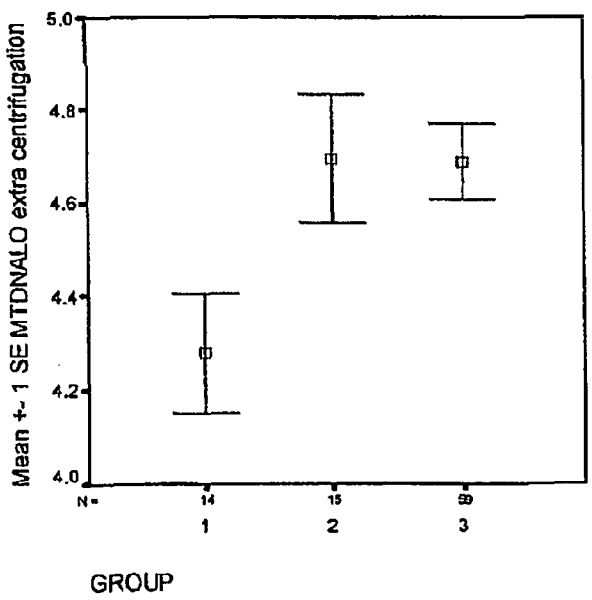
Figure 19:
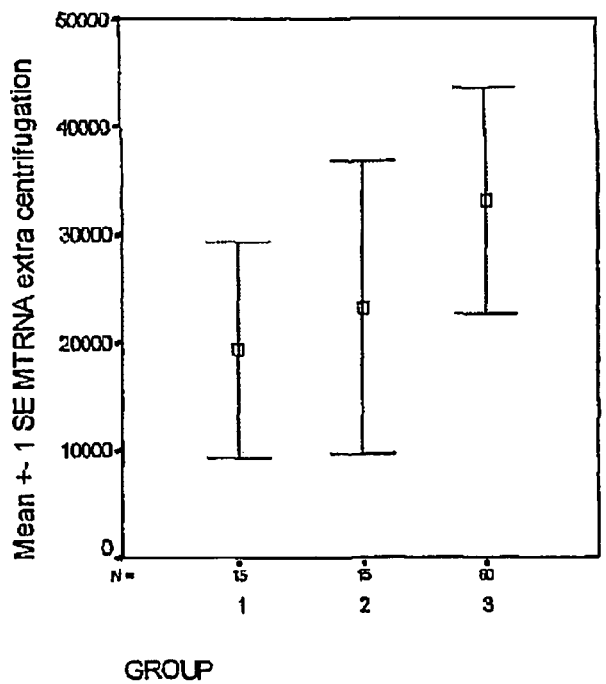
Figure 19:
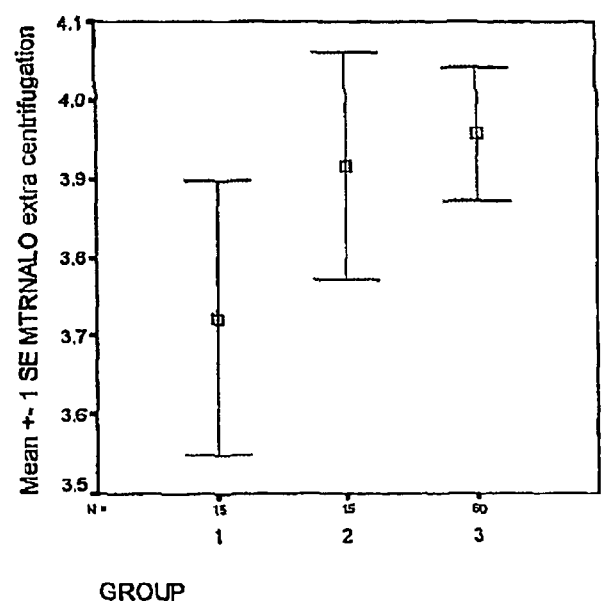

The results are summarized in FIGS. 18 (mtDNA) and 19 (mtRNA). A clear increase in copy numbers of mtDNA and mtRNA is observed in patients with metastasizing disease, compared to both other groups.

Figure 20:
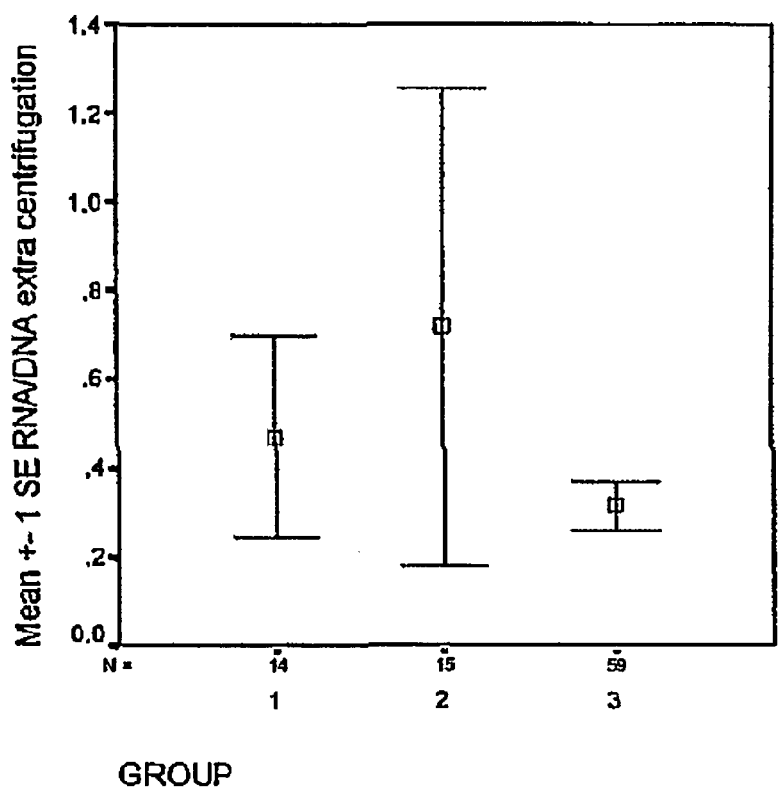
FIG. 20 shows mtRNA/mtDNA ratios in centrifugated prostate cancer samples.

Also, the ratio of mtRNA/mtDNA is analyzed in the centrifuged plasma samples (FIG. 20). From this figure, it is clear that with our assays, it is possible to discriminate between patients with and without cancer.

In summary, we show that with the tests described in these examples, it is possible to discriminate between patients with or without tumors (e.g., Example 5, FIG. 14). With these tests, it is also possible to discriminate between patients with and without metastasis (e.g., Example 6, FIG. 17).

Example 8

Renal Cell Carcinoma (RCC)

Plasma was isolated using a BD Vacutainer® CPT™ Cell Preparation Tube with Sodium Citrate. Two of those tubes were drawn, the first tube was discarded to avoid contamination of the blood draw. Plasma was isolated from 15 healthy volunteers and 35 patients with RCC. The plasma samples used in this example were already subjected to an extra centrifugation at 3400 rcf before storing at −80° C. Therefore, the samples were not subjected to centrifugation after thawing. One hundred µl of the plasma was put in 900 µL6. Then, the nucleic acids were isolated and mtDNA and mtRNA were quantified as described in the previous examples.

Figure 21:
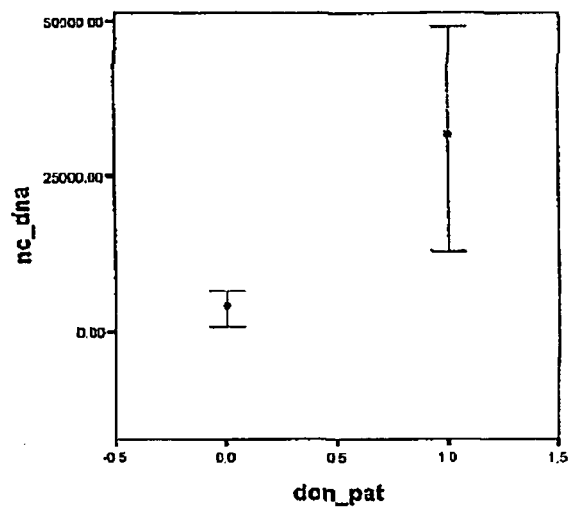
FIGS. 21 and 22 show mtDNA (FIG. 21) and mtRNA (FIG. 22) quantification in healthy volunteers and in patients with renal cell carcinoma (RCC).
Figure 21:
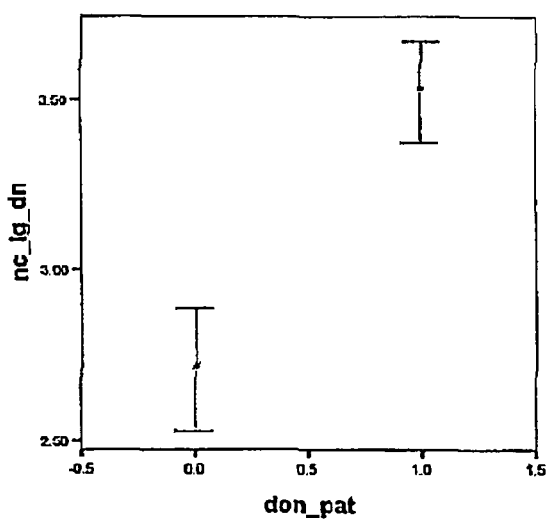
Figure 22:
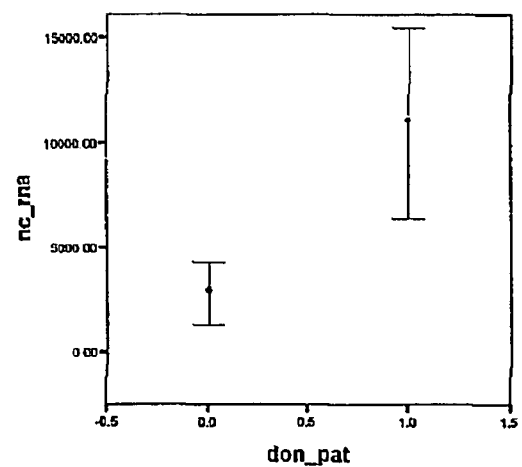
Figure 22:
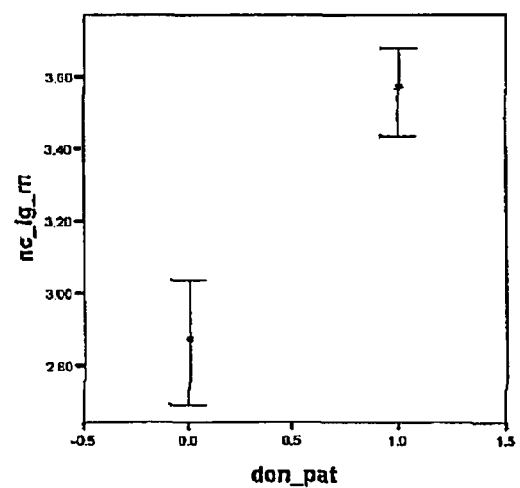

The results are summarized in FIGS. 21 (mtDNA) and 22 (mtRNA). A clear increase in copy numbers of mtDNA and mtRNA is observed in patients with metastasizing disease, compared to both other groups. From these figures, it is clear that with our assays, it is possible to discriminate between patients with and without cancer.

Figure 23:
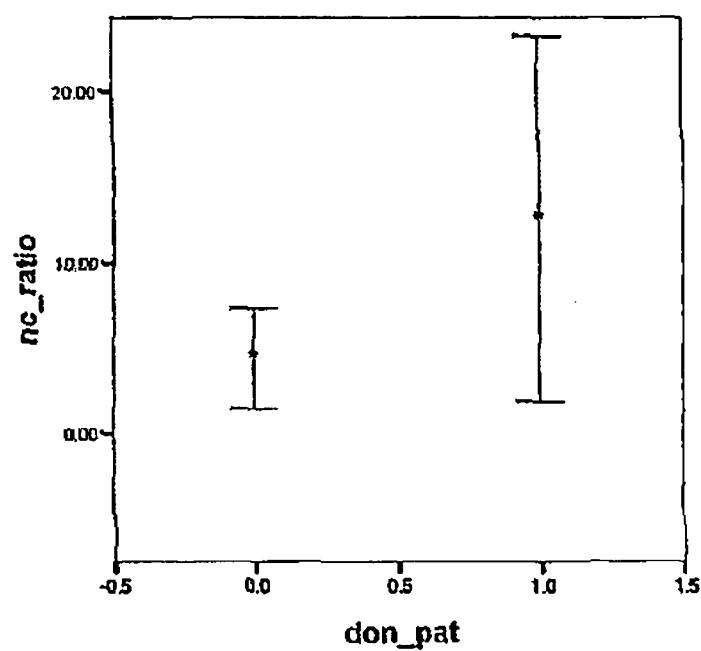
FIG. 23 shows mtRNA/mtDNA ratios in centrifugated plasma samples.

Also, the ratio of mtRNA/mtDNA is analyzed in the centrifuged plasma samples (FIG. 23).

Example 9

Prostate Cancer

Plasma Isolation

Plasma was isolated from the blood of 78 patients with various stages of disease and twelve patients with benign prostate disease within two hours after draw, using a BD Vacutainer® Tube with Sodium Citrate (Becton Dickinson, BD Biosciences, Mountain View, Calif.). Plasma was centrifuged at 1700 rcf for 15 minutes after which the supernatant was stored at −80° C. After thawing, a part of the plasma samples was used directly (one-spin plasma). To prepare the two-spin plasma samples, 150 µl of plasma was centrifuged at 3400 rcf. for 15 minutes at room temperature. The upper 100 µl was transferred to a new tube before isolation.

Nucleic Acid Isolation

One hundred µl of plasma was added to a 1.5 ml Eppendorf tube containing 900 µl lysis buffer. The nucleic acids now present in the lysis buffer were further purified with the method described by Boom et al. (1990). The isolated nucleic acids were eluted in 50 µl elution buffer.

NASBA Amplification

Standard NASBA nucleic acid amplification reactions were performed in a 20 µl reaction volume and contained: 40 mM Tris-pH 8.5, 90 mM KCl, 12 mM $MgCl_2$, 5 mM dithiotreitol, 1 mM dNTPs (each), 2 mM rNTPs (each), 0.2 µM primer P1, 0.2 µM primer P2, 0.05 µM molecular beacon (Table 1), 375 mM sorbitol, 0.105 µg/µl bovine serum albumin, 6.4 units AMV RT, 32 units T7 RNA polymerase, 0.08 units RNase H and input nucleic acid. For the amplification of RNA, the complete mixture (except the enzymes) was, prior to adding the enzymes, heated to 65° C. for three minutes in order to denature any secondary structure in the RNA and to allow the primers to anneal. In the case of DNA, 2 units of MSP I were added and the mix was incubated at 37° C. for 15 minutes, followed by denaturation at 95° C. for three minutes. After cooling the mixtures to 41° C., the enzymes were added. The amplification took place at 41° C. for 90 minutes in a thermostated fluorimeter (RetinAlyzer or EasyQ® Reader) and the fluorescent signal of the molecular beacon probe was measured every 45 seconds.

To achieve quantification, a dilution series of target sequence was amplified and the time points at which the reactions became positive (the time to positivity, TTP) were plotted against the input amounts of nucleic acids. This way, a calibration curve was created that could be used to determine the input amount of the reactions with unknown amounts of input by interpolation of their TTP values. All amplifications were performed in duplicate. The average of these duplicate amplifications was considered as the value for the sample. If the difference between duplicate amplifications was >0.5 log value, the amplification for that sample was repeated.

Results

There is a strong correlation between one-spin and two-spin samples (mtDNA: r=0.67, p=0.00; and mtRNA: r=0.59, p=0.00). One-spin mtDNA and mtRNA copies were not influenced by cancer, only prior treatment with radiotherapy and immunotherapy led to significant lower amounts of mtDNA and mtRNA (mtDNA p=0.01 and mtRNA p=0.04; mtDNA p=0.04 only; results not shown).

Figure 24:
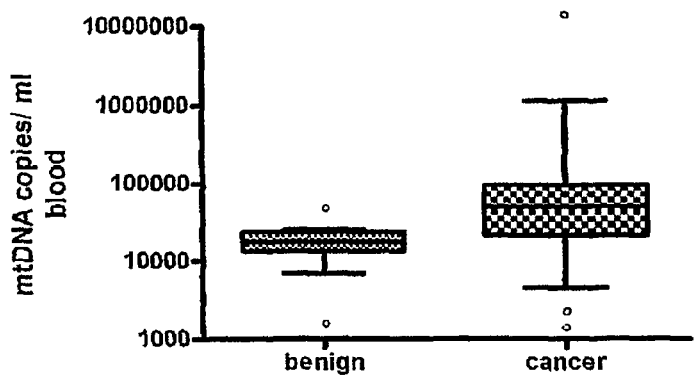
FIG. 24 shows mtDNA and mtRNA in benign prostate disease and prostate cancer.
Figure 24:
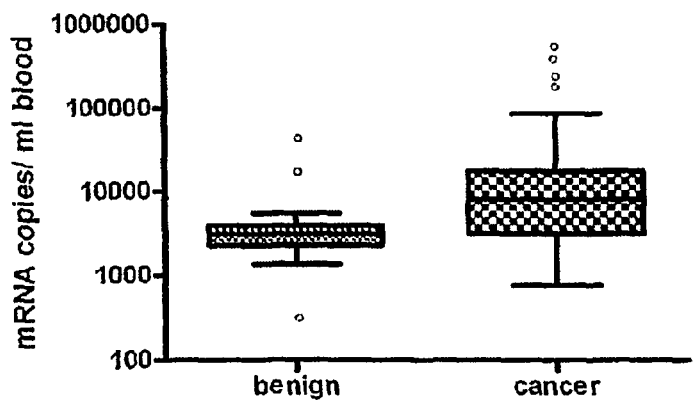

Two-spin plasma showed differential amounts of mtDNA and mtRNA in prostate cancer compared to benign disease (FIG. 24). Further analysis was, therefore, done with two-spin plasma.

Figure 25:
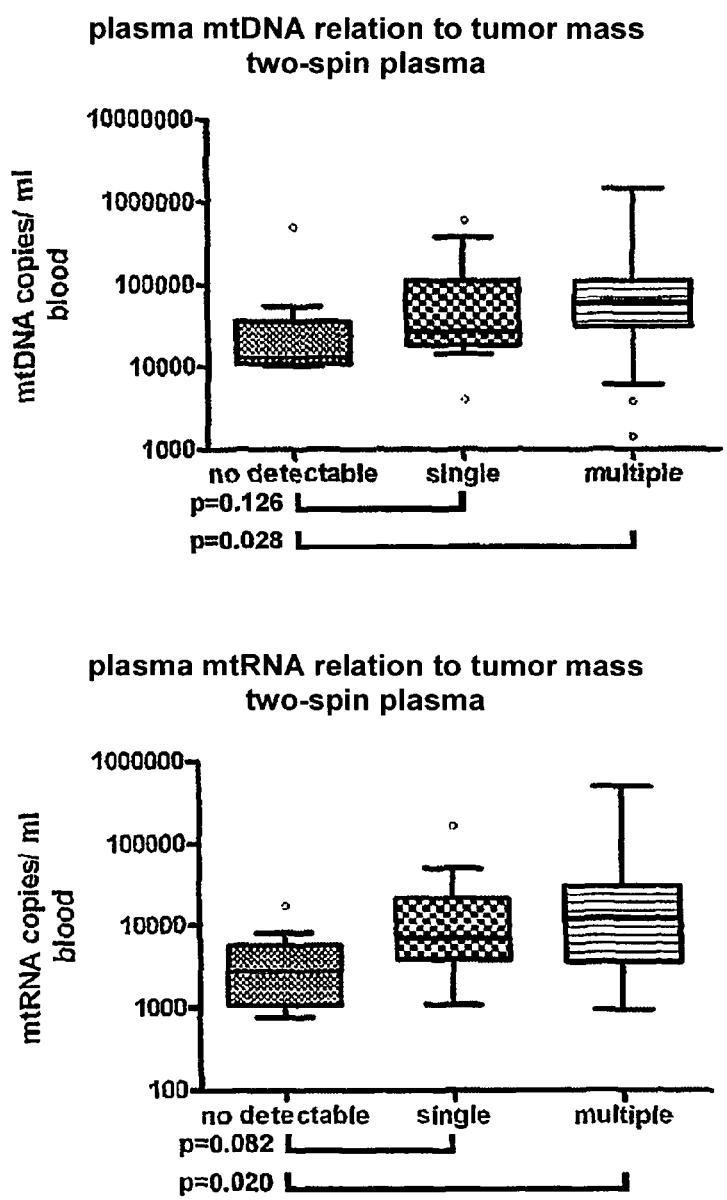
FIG. 25 shows mtDNA and mtRNA in patients stratified to number of tumors.

Patients were divided into three groups: the first consisting of nine patients without detectable tumor mass, the second group consisting of 13 patients with only a single tumor and the third group consisted of 43 patients with multiple tumors. There is an increase in the mtRNA and mtDNA copy number in the plasma of patients with single tumors compared to patients without detectable tumor mass (p=0.082 and p=0.126). Patients with multiple tumors have a significant increase in mtRNA and mtDNA copies compared to patients without macroscopic tumor lesions (p=0.020 and p=0.028). There is no significant increase in copy number between patients with multiple tumors compared to a single tumor (FIG. 25).

Figure 26:
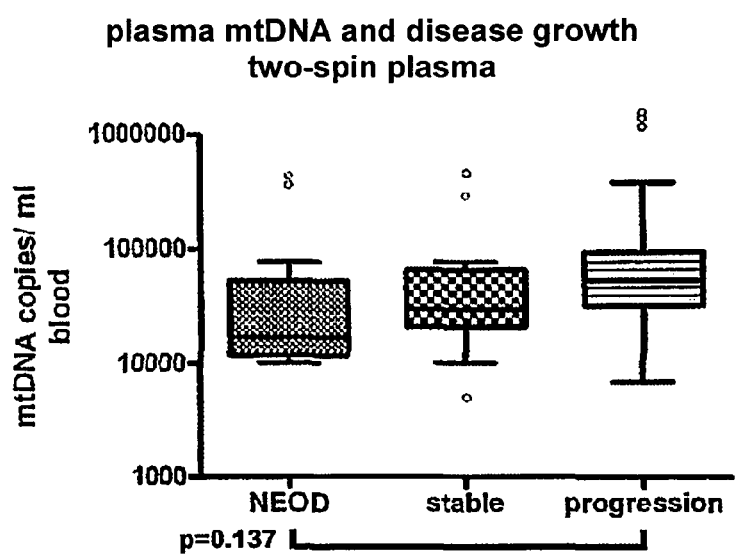
FIG. 26 shows mtDNA and mtRNA in patients stratified to tumor growth.
Figure 26:
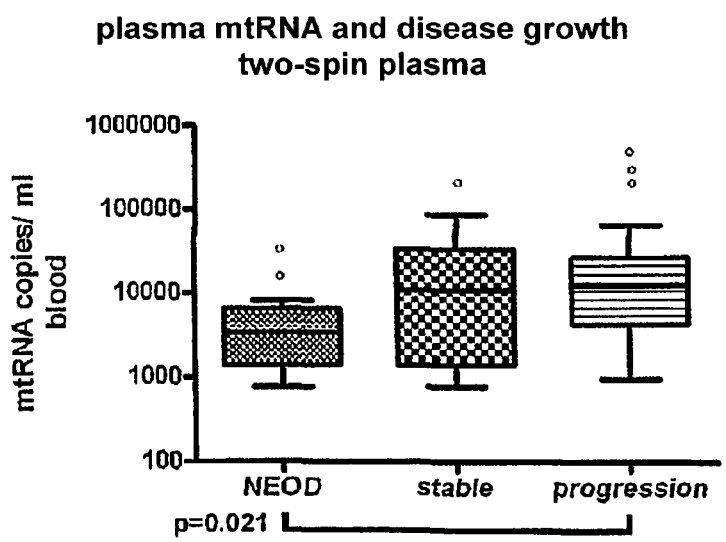

Patients are categorized in three groups according to their tumor growth as determined by changes in radiological examination and laboratory parameters before and after blood draw combined with clinical evidence. The first group consisted of twelve patients who had either no evidence of disease, regressive disease or cancer remission (NEOD). The second group (stable) consisted of 13 patients who had no changes in tumor growth and/or no changes in tumor markers. The third group (progression) consisted of 42 patients who had an increase in tumor size and/or increase in tumor markers. Patients with progressive disease have an increased mtRNA (p=0.021) but no mtDNA (p=0,137), compared to patients with NEOD. Patients with stable disease do not have increased intRNA or mtDNA in comparison with NEOD (p=0.288 and p=0.608). There is also no difference between patients with progressive disease and stable disease (p=0.553 and p=0.388) (FIG. 26).

There was a significant correlation of mtDNA and mtRNA with alkaline phosphatase (a marker for bone metastases/cell death in bones: r=0.36, p=0.01 and r=0.37, p=0.01) and PSA (prostate specific antigen: r=0.28, p=0.02 and r=0.33, p=0.00).

Figure 27:
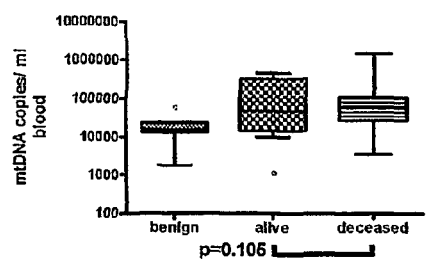
FIG. 27 shows mtDNA and mtRNA in survivors and non-survivors.
Figure 27:
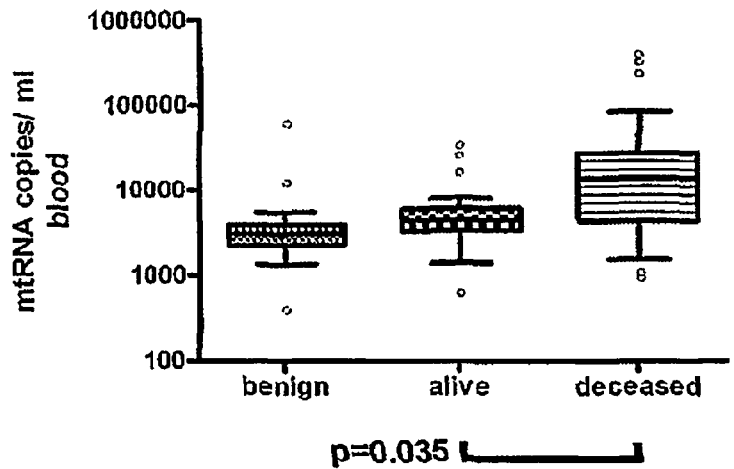

Clinical information of 55 patients regarding survival is known thus far. Patients were followed for approximately three years after blood draw and survival and mtDNA and mtRNA was evaluated. Patients that are deceased because of their disease (n=39) have a 4.8-fold increase in mtRNA copy number at time of blood draw compared to patients that are still alive (n=16) at end-point of follow-up (FIG. 27).

Figure 28:
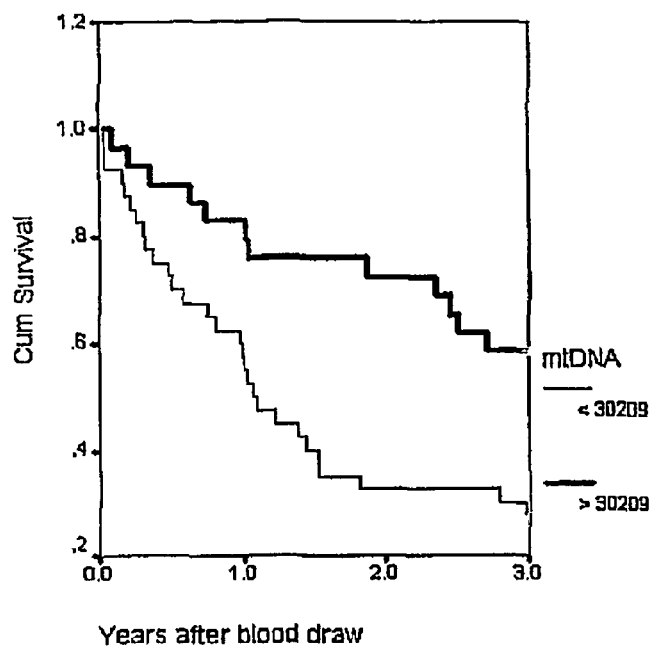
FIG. 28 shows three-year survival in patients with higher versus lower mtDNA and mtRNA copy numbers.
Figure 28:
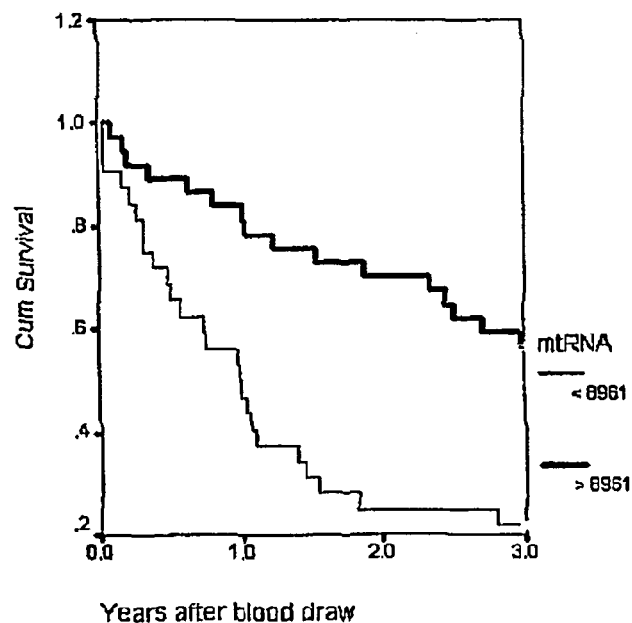

Based on the mtDNA and mtRNA copy numbers at time of diagnosis, a prediction can be made about the changes of survival of a patient. In FIG. 28, patients are divided into two groups, based on mtDNA copy numbers (higher or lower than 30209 copies) or mtRNA copy numbers (higher or lower than 8961 copies).

These data suggest that mtDNA and mtRNA have a diagnostic value and predictive value in prostate cancer management.

Example 10

Breast Cancer

Sample Preparation

Citrate blood has been collected from 36 patients with various stages of breast cancer and ten healthy controls of women with benign breast disorders. Plasma was isolated as described in Example 9. From one-spin plasma and two-spin plasma, nucleic acids were isolated and mtDNA and mtRNA were quantified by real-time NASBA assays as described in Example 9.

Figure 29:
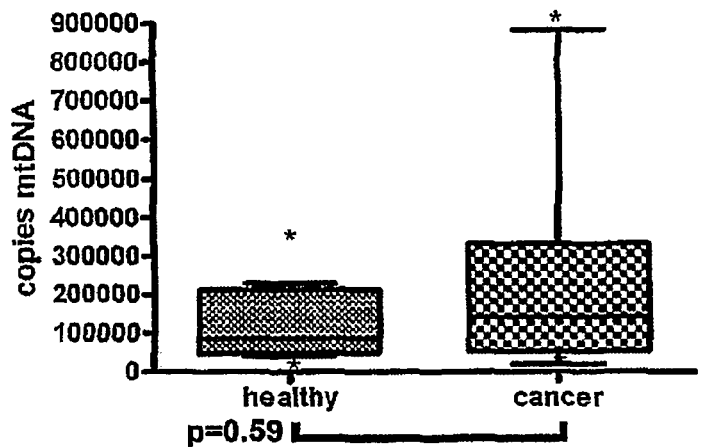
FIG. 29 shows mtDNA and mtRNA in healthy individuals with benign breast disorders and in patients having breast cancer.
Figure 29:
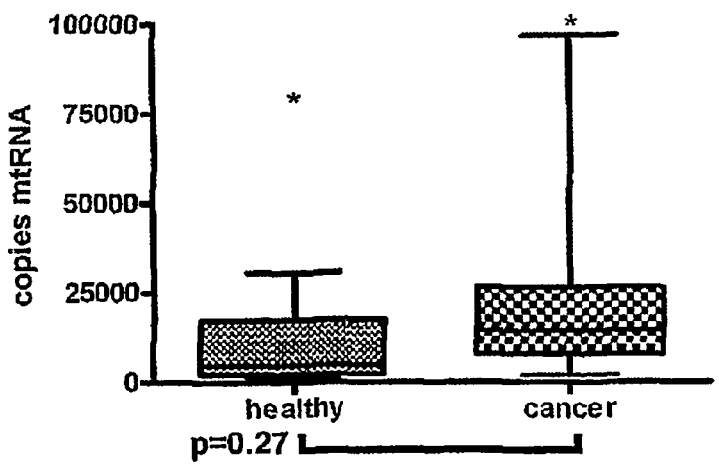

The heterogeneous breast cancer group did not have significantly increased mtDNA or mtRNA content in the one-spin plasma compared to the benign controls. In the two-spin plasma, increased mtDNA or mtRNA copy numbers were observed, although the increase was not significant (FIG. 29).

Figure 30:
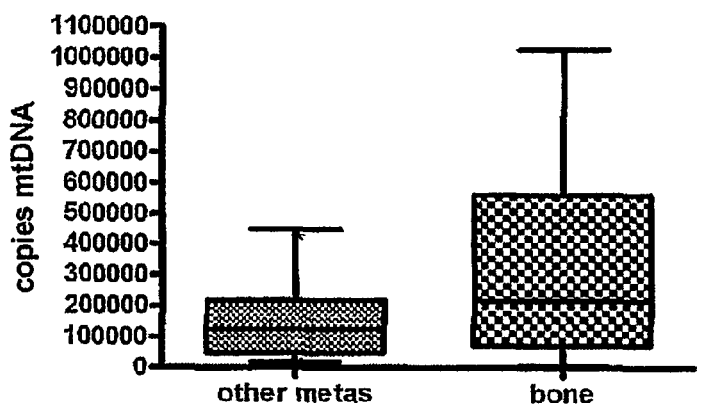
FIG. 30 shows mtDNA and mtRNA in patients with bone metastasis.
Figure 30:
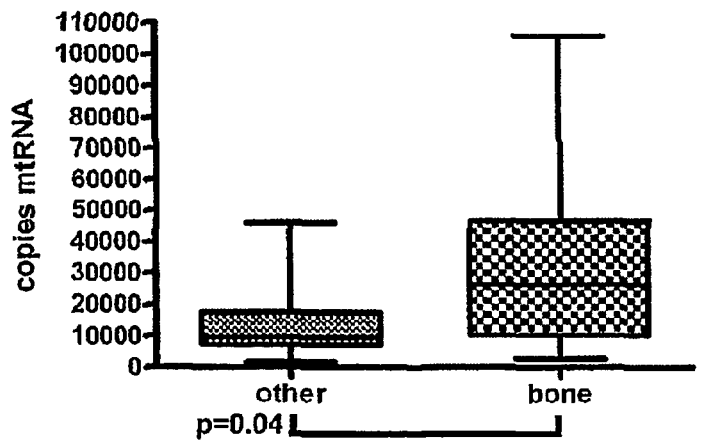

Patients with bone metastasis had increased amounts of mtRNA and mtDNA transcripts (mtRNA 2.5-fold mean increase; mtDNA 2.3-fold mean increase) (FIG. 30).

Figure 31:
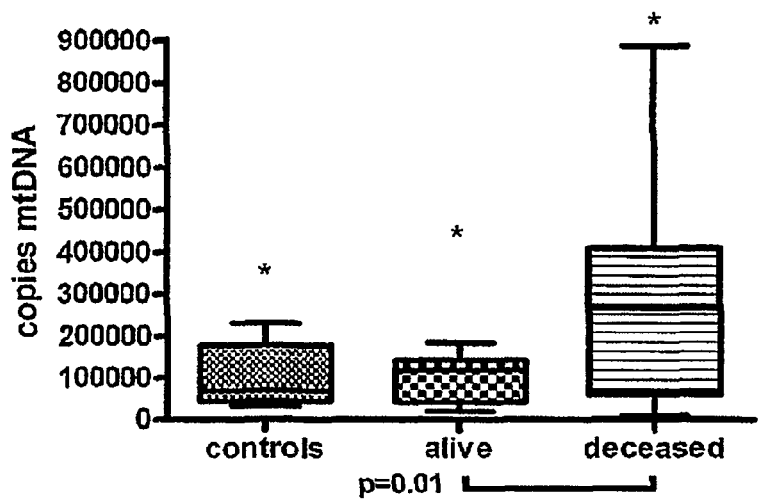
FIG. 31 shows mtDNA and mtRNA copy numbers in survivors and non-survivors.
Figure 31:
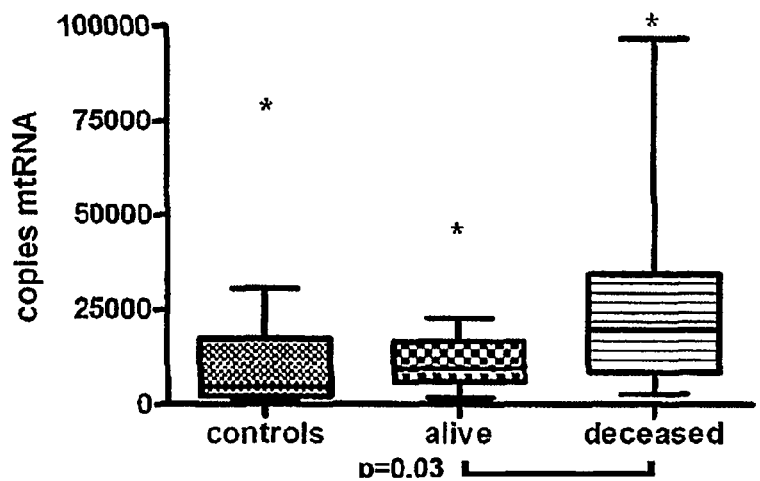

After three years following blood collection, 18 patients had died due to tumor progression and the other 18 patients had complete, partial remission or stable disease. At the moment of blood draw, patients with good prognosis have similar mtRNA and mtDNA values as healthy controls but patients with bad prognosis had a 2.5-fold lower level of plasma mtRNA and a three-fold lower level of plasma mtDNA than the patient group with a bad outcome (FIG. 31).

Figure 32:
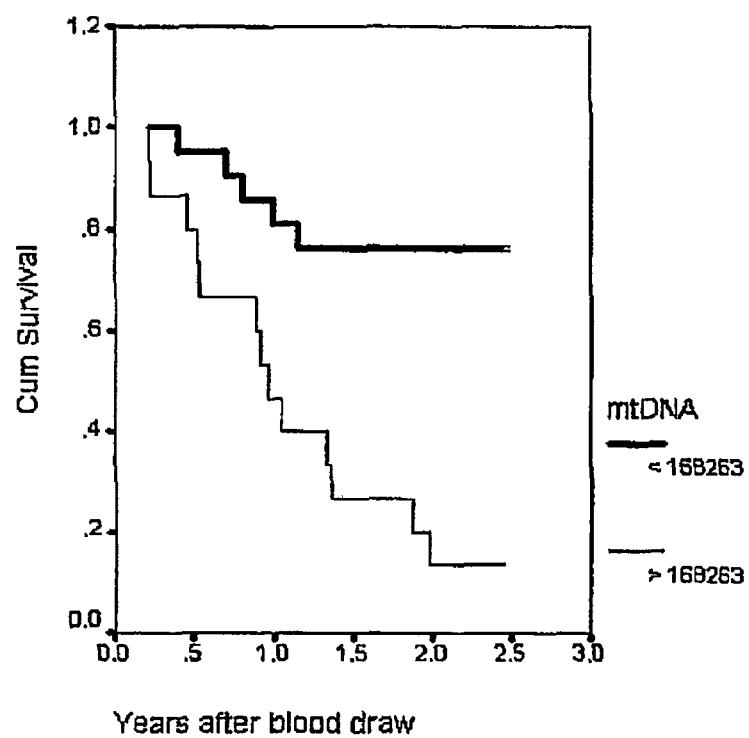
FIG. 32 shows a Kaplan-Meier survival analysis in patients with breast cancer for high or low plasma mtDNA.

ROC-analysis indicates that a cut-off of 168263 mtDNA copies is an indicator of a poor 2.5-year survival (outcome death with a sensitivity of 72% and a specificity of 89%; cut-off value of 20100 mtDNA copies has a sensitivity 67% and specificity 94%) (FIG. 32).

Example 11

Renal Cell Cancer (RCC)

Sample Preparation

Citrate blood has been collected from 31 patients with renal cell cancer (RCC) and 15 healthy controls. Plasma was isolated as described in Example 9. From two-spin plasma, nucleic acids were isolated and mtDNA and mtRNA were quantified by real-time NASBA assays as described in Example 9.

Figure 33:
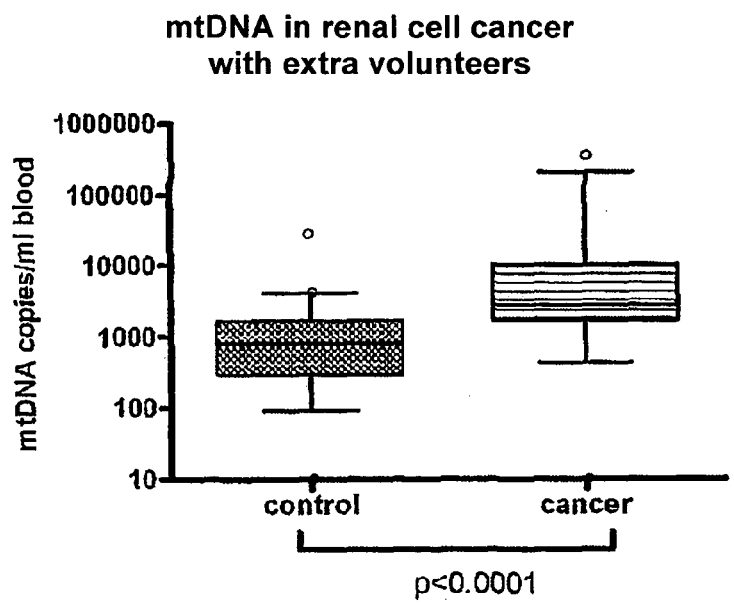
FIG. 33 shows mtDNA and mtRNA in plasma from healthy controls and RCC patients.
Figure 33:
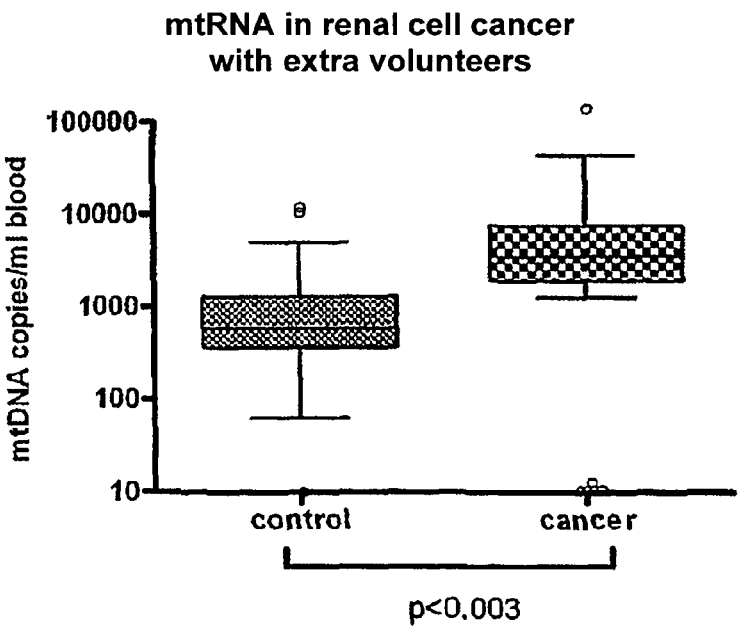

As is clear from FIG. 33, patients with RCC have significantly higher mtDNA and mtRNA copy numbers in plasma as compared to healthy controls.

Figure 34:
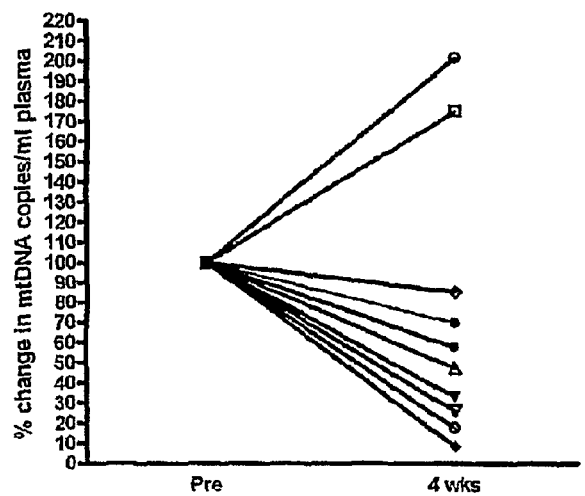
FIG. 34 shows mtDNA and mtRNA copy numbers in plasma from healthy controls and RCC patients.
Figure 34:
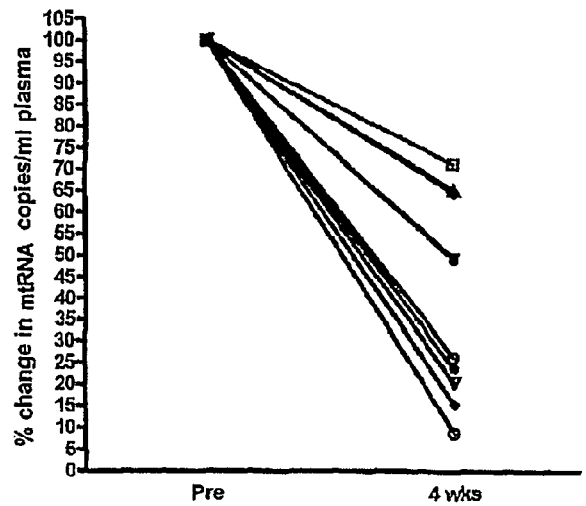

From a number of patients, a follow-up sample after four weeks of treatment was available. As shown in FIG. 34, a clear change in mtDNA and mtRNA copy numbers is observed after therapy.

TABLE 1

Sequences of primers and probes used.

| Name | Sequencer |
|------|-----------|
| U1A P1 | 5' AAT TCT AAT ACG ACT CAC TAT AGG GAG AGG CCC GGC ATG TGG TGC ATA A 3' (SEQ ID NO: 1) |
| U1A P2 | 5' TGC CCC TCT TTC TGG GTG TT 3' (SEQ ID NO: 2) |
| U1A MB | 5' CGC ATG CTG TAA CCA CGC ACT CTC CTC GCA TGC G 3' (SEQ ID NO: 3) |

TABLE 1-continued

Sequences of primers and probes used.

| Name | Sequencer |
|---|---|
| mtRNA P1 | 5' *AAT TCT AAT ACG ACT CAC TAT AGG* GAG AGG AGA CAC CTG CTA GGT GTA A 3' (SEQ ID NO: 4) |
| mtRNA P2 | 5' GGT GCC CCC GAT ATG GCG TTC C 3' (SEQ ID NO: 5) |
| mtRNA MB | 5' CGA TCC AAG GAC AAG GCG TTC ACA GGA TCG 3' (SEQ ID NO: 6) |
| mtDNA P1 | 5' *AAT TCT AAT ACG ACT CAC TAT AGG* GAA GAA CCC GGC TCT GCC ATC TTA A 3' (SEQ ID NO: 7) |
| mtDNA P2 | 5' GTA ATC CAG GTC GGT TTC TA 3' (SEQ ID NO: 8) |
| mtDNA MB | 5' CGT ACG TGA TAT CAT CTC AAC TTA GTA TCG TAC G 3' (SEQ ID NO: 9) |

The T7 promoter part of primer P1 sequences is shown in italics, the stem sequences of the molecular beacon probes (MB) are shown in bold. The molecular beacon probes were labeled at the 3' end with DABCYL (the quencher) and at the 5' end with a fluorescent label, which is ROX in all cases.

NOTE: The DNA specificity of the mtDNA primers is assured by locating the two primers in the coding regions of adjacent genes. It is not possible to choose mtRNA primers in such a way that it is not possible (at least in theory) to also amplify also mtDNA. Amplification of RNA with the mtRNA primers is stimulated by performing the denaturation at 65° C., whereas DNA is denatured at 95° C. The RNA specificity of the mtRNA primers is illustrated in an experiment using thrombocytes. It is known from literature that thrombocytes contain mtDNA, but no (or very little) mtRNA. When the nucleic acids isolated from thrombocytes are amplified with the mtRNA assay, no signal is found (results not shown).

TABLE 2

Treatment of plasma samples.

| sample no. | freeze/thaw cycles | centrifugation |
|---|---|---|
| 1, 2 | 0 | no centrifugation |
| 3, 4 | 0 | 15 minutes at 3400 rcf |
| 5, 6 | 1 | no centrifugation |
| 7, 8 | 1 | 15 minutes at 3400 rcf |
| 9, 10 | 2 | no centrifugation |
| 11, 12 | 2 | 15 minutes at 3400 ref |

REFERENCES

Boom R., C. J. Sol, M. M. Salimans, C. L. Jansen, P. M. Wertheim-van Dillen, J. Van der Noordaa. Rapid and simple method for purification of nucleic acids. *J. Clin. Microbiol.* 28:495-503, 1990.

What is claimed is:

1. A method for determining whether an individual is suffering from ovarian cancer, breast cancer, prostate cancer, or renal cell carcinoma, the method comprising:
    selecting an individual suffering from or suspected of suffering from ovarian cancer, breast cancer, prostate cancer, or renal cell carcinoma or from metastasized ovarian cancer, breast cancer, prostate cancer or from metastasized renal cell carcinoma;
    centrifuging a sample of body fluid of an individual, wherein the body fluid is selected from the group consisting of plasma and serum, wherein the sample is centrifuged at 1600-1800 g,
    then centrifuging the sample at 2500-4500 g to form a centrifuged sample, and
    conducting a nucleic acid amplification step on the centrifuged sample to determine the relative amount of cell-free mitochondrion-bound nucleic acid.

2. The method according to claim 1, wherein an amount of cell-free mitochondrion-bound nucleic acid is determined by determining an amount of total mitochondrion-bound nucleic acid and an amount of cellular mitochondrion-bound nucleic acid in said sample and subtracting the amount of cellular mitochondrion-bound nucleic acid from the amount of total mitochondrion-bound nucleic acid.

3. The method according to claim 1, wherein said nucleic acid comprises RNA.

4. The method according to claim 1, wherein the sample is a sample obtained from the individual after initiation of treatment for ovarian cancer, breast cancer, prostate cancer, or renal cell carcinoma.

5. The method according to claim 1, wherein said sample is essentially cell free.

6. The method according to claim 1, wherein said sample is centrifuged under conditions that preferentially sediment cells when compared to cell-free mitochondria.

7. The method according to claim 6, wherein said sample is centrifuged at 1700×g.

8. The method according to claim 7, wherein said sample is centrifuged at 1700×g, followed by a centrifugation at 3400×g.

9. The method according to claim 1, further comprising freezing and thawing said sample prior to determining cell-free mitochondrion-bound nucleic acid therein.

10. The method according to claim 1, wherein said sample is frozen and thawed in between centrifugation at 1600-1800 g and centrifugation at 2500-4500 g.

11. The method according to claim 1, wherein the cell-free mitochondrion-bound nucleic acid is determined relative to another parameter in said sample.

12. The method according to claim 11, wherein said another parameter comprises nuclear nucleic acid.

13. The method according to claim 11, wherein said another parameter comprises determining an alkaline phosphatase parameter, a PSA parameter for the individual, or both.

14. The method according to claim 12, wherein said nuclear nucleic acid is determined in a sample comprising essentially cell-free mitochondrion-bound nucleic acid and wherein said nuclear nucleic acid is determined as a value for the relative freeness of the sample of cells.

15. The method according to claim 1, wherein said amplification step comprises one of the following amplification methods: PCR, NASBA, TMA, SDA, LCR, bDNA, and rolling circle amplification.

16. The method according to claim 1, wherein said sample was dried and stored on a solid carrier prior to determining cell-free mitochondrion-bound nucleic acid.

17. The method according to claim 16, wherein said solid carrier is paper.

18. The method according to claim 1, further comprising determining cellular mitochondrion-bound nucleic acid.

19. The method according to claim 1, further comprising determining a non-mitochondrion-bound nucleic acid in said sample.

20. The method according to claim 19, wherein said non-mitochondrion-bound nucleic acid is a control nucleic acid present in or provided to said sample.

21. The method according to claim 20, wherein said control nucleic acid and cell-free mitochondrion-bound nucleic acid is amplified in one amplification step.

22. The method according to claim 1, wherein the sample is interacted with a primer, a primer pair or a probe.

23. The method according to claim 22, wherein said primer, primer pair or probe is a U1A primer, primer pair or probe.

24. The method according to claim 22, wherein said primer, primer pair or probe is a mtRNA primer, primer pair or probe.

25. The method according to claim 22, wherein said primer, primer pair or probe is a mtDNA primer, primer pair or probe.

26. A method for determining whether an individual is suffering from ovarian cancer, breast cancer, prostate cancer, or renal cell carcinoma, the method comprising:
    selecting an individual suffering from or suspected of suffering from ovarian cancer, breast cancer, prostate cancer, or renal cell carcinoma, or from metastasized ovarian cancer, breast cancer, prostate cancer or from metastasized renal cell carcinoma,
    centrifuging a sample from an individual, said sample comprising serum or plasma at 1600-1800 g,
    then centrifuging at 2500-4500 g to form a centrifuged sample, and
    interacting the centrifuged sample with means for quantitating cell-free mitochondrion-bound nucleic acid in a sample from the individual.

27. A method for determining whether an individual suffering from ovarian cancer, breast cancer, prostate cancer, or renal cell carcinoma has one or alternatively multiple tumor sites, the method comprising:
    selecting an individual suffering from ovarian cancer, breast cancer, prostate cancer, or renal cell carcinoma,
    centrifuging a sample of body fluid of the individual, wherein the body fluid is selected from the group consisting of plasma and serum, wherein the sample is centrifuged at 1600-1800 g, then centrifuging the sample at 2500-4500 g to form a centrifuged sample, and conducting a nucleic acid amplification step on the centrifuged sample to determine the relative amount of cell-free mitochondrion-bound nucleic acid.

28. A method for determining whether an individual suffering from ovarian cancer, breast cancer, prostate cancer, or renal cell carcinoma is responding to treatment for the cancer or carcinoma, the method comprising:

selecting an individual suffering from ovarian cancer, breast cancer, prostate cancer, or renal cell carcinoma, centrifuging a sample of body fluid of the individual, wherein the body fluid is selected from the group consisting of plasma and serum, wherein the sample is centrifuged at 1600-1800 g, then centrifuging the sample at 2500-4500 g to form a centrifuged sample, and conducting a nucleic acid amplification step on the centrifuged sample to determine the relative amount of cell-free mitochondrion-bound nucleic acid.

29. A method for determining a survival prognosis for an individual suffering from ovarian cancer, breast cancer, prostate cancer or from renal cell carcinoma, the method comprising:

selecting an individual suffering from ovarian cancer, breast cancer, prostate cancer, or renal cell carcinoma, centrifuging a sample of body fluid of the individual, the body fluid selected from the group consisting of plasma and serum, wherein the sample is centrifuged at 1600-1800 g, then centrifuging the sample at 2500-4500 g to form a centrifuged sample, and conducting a nucleic acid amplification step on the centrifuged sample to determine the relative amount of cell-free mitochondrion-bound nucleic acid.

* * * * *

SEQUENCE LISTING

<160> NUMBER OF SEQ ID NOS: 9

<210> SEQ ID NO 1
<211> LENGTH: 49
<212> TYPE: DNA
<213> ORGANISM: Artificial Sequence
<220> FEATURE:
<223> OTHER INFORMATION: Chemically synthesized - U1A P1

<400> SEQUENCE: 1
aattctaata cgactcacta tagggagagg cccggcatgt ggtgcataa        49

<210> SEQ ID NO 2
<211> LENGTH: 20
<212> TYPE: DNA
<213> ORGANISM: Artificial Sequence
<220> FEATURE:
<223> OTHER INFORMATION: Chemically synthesized - U1A P2

<400> SEQUENCE: 2
tgcgcctctt tctgggtgtt        20

<210> SEQ ID NO 3
<211> LENGTH: 34
<212> TYPE: DNA
<213> ORGANISM: Artificial Sequence
<220> FEATURE:
<223> OTHER INFORMATION: Chemically synthesized - U1A MB

<400> SEQUENCE: 3
cgcatgctgt aaccacgcac tctcctcgca tgcg                        34

<210> SEQ ID NO 4
<211> LENGTH: 49
<212> TYPE: DNA
<213> ORGANISM: Artificial Sequence
<220> FEATURE:
<223> OTHER INFORMATION: Chemically synthesized - mtRNA P1

<400> SEQUENCE: 4
aattctaata cgactcacta tagggagagg agacacctgc taggtgtaa        49

<210> SEQ ID NO 5
<211> LENGTH: 22
<212> TYPE: DNA
<213> ORGANISM: Artificial Sequence
<220> FEATURE:
<223> OTHER INFORMATION: Chemically synthesized - mtRNA P2

<400> SEQUENCE: 5
ggtgcccccg atatggcgtt cc                                     22

<210> SEQ ID NO 6
<211> LENGTH: 30
<212> TYPE: DNA
<213> ORGANISM: Artificial Sequence
<220> FEATURE:
<223> OTHER INFORMATION: Chemically synthesized - mtRNA MB

<400> SEQUENCE: 6
cgatccaagg acaaggcgtt cacaggatcg                             30

<210> SEQ ID NO 7
<211> LENGTH: 49
<212> TYPE: DNA
<213> ORGANISM: Artificial Sequence
<220> FEATURE:
<223> OTHER INFORMATION: Chemically synthesized - mtDNA P1

<400> SEQUENCE: 7
aattctaata cgactcacta tagggaagaa ccgggctctg ccatcttaa        49

<210> SEQ ID NO 8
<211> LENGTH: 20
<212> TYPE: DNA
<213> ORGANISM: Artificial Sequence
<220> FEATURE:
<223> OTHER INFORMATION: Chemically synthesized - mtDNA P2

<400> SEQUENCE: 8
gtaatccagg tcggtttcta                                        20

<210> SEQ ID NO 9
<211> LENGTH: 34
<212> TYPE: DNA
<213> ORGANISM: Artificial Sequence
<220> FEATURE:

```
<223> OTHER INFORMATION: Chemically synthesized - mtDNA MB

<400> SEQUENCE: 9
cgtacgtgat atcatctcaa cttagtatcg tacg                                34
```